United States Patent
Chuang et al.

(10) Patent No.: US 9,572,527 B2
(45) Date of Patent: Feb. 21, 2017

(54) SKIN PERMEATION DEVICE FOR ANALYTE SENSING OR TRANSDERMAL DRUG DELIVERY

(71) Applicant: Echo Therapeutics, Inc., Franklin, MA (US)

(72) Inventors: Han Chuang, Canton, MA (US); Juan P. Eslava, Boylston, MA (US); James P. Hurley, Foxboro, MA (US); Debashis Ghosh, Ashland, MA (US); Keith Krystyniak, Chelmsford, MA (US); Scott C. Kellogg, Mattapoisett, MA (US)

(73) Assignee: Echo Therapeutics, Inc., Iselin, NJ (US)

( * ) Notice: Subject to any disclaimer, the term of this patent is extended or adjusted under 35 U.S.C. 154(b) by 0 days.

(21) Appl. No.: 13/746,673

(22) Filed: Jan. 22, 2013

(65) Prior Publication Data

US 2013/0137951 A1 May 30, 2013

Related U.S. Application Data

(63) Continuation of application No. 12/110,034, filed on Apr. 25, 2008, now Pat. No. 8,386,027.

(Continued)

(51) Int. Cl.
*A61B 5/05* (2006.01)
*A61B 5/00* (2006.01)
(Continued)

(52) U.S. Cl.
CPC ............ *A61B 5/442* (2013.01); *A61B 5/0531* (2013.01); *A61B 17/54* (2013.01); *A61B 18/20* (2013.01);
(Continued)

(58) Field of Classification Search
CPC .......... A61N 1/0412; A61N 1/08; A61N 1/30; A61N 1/325; A61N 1/327; A61N 1/328; A61M 2037/0007; A61M 2230/65; A61B 5/0531; A61B 2017/00747; A61B 2017/00761
(Continued)

(56) References Cited

U.S. PATENT DOCUMENTS 2,887,112 A 5/1959 Smith
3,508,540 A 4/1970 Cavallari, et al.
(Continued)

FOREIGN PATENT DOCUMENTS

CA 2226176 1/1997
CA 2212826 7/1997
(Continued)

OTHER PUBLICATIONS

Agrawal, et al., "The effects of ultrasound irradiation on a biodegradable 50-50% copolymer of polylactic and polyglycolic acids", *J Biomed Mater Res.*, 28(8):851-9 (1994).
(Continued)

*Primary Examiner* — Devin Henson
(74) *Attorney, Agent, or Firm* — Pabst Patent Group LLP

(57) ABSTRACT

Devices, systems, kits and methods for increasing the skin's permeability controlled by measured skin electrical parameter are described herein. They may be used for transdermal drug delivery and/or analyte extraction or measurement. The controlled abrasion device contains (i) a hand piece, (ii) an abrasive tip, (iii) a feedback control mechanism, (iv) two or more electrodes, and (v) an electrical motor. The feedback control mechanism may be an internal feedback control mechanism or an external feedback control. The kit contains the controlled abrasion-device, one or more abrasive tips, optionally with a wetting fluid. The method for increasing
(Continued)

the skin's permeability requires applying the controlled abrasion device to a portion of the skin's surface for a short period of time, until the desired level of permeability is reached. Then the abrasion device is removed, and a drug delivery composition or device or an analyte sensor is applied to the treated site.

20 Claims, 11 Drawing Sheets

Related U.S. Application Data

(60) Provisional application No. 60/914,552, filed on Apr. 27, 2007.

(51) Int. Cl.
*A61B 5/053* (2006.01)
*A61B 17/54* (2006.01)
*A61B 18/20* (2006.01)
*A61N 1/04* (2006.01)
*A61N 1/32* (2006.01)
*A61B 17/00* (2006.01)
*A61B 17/32* (2006.01)
*A61B 18/00* (2006.01)
*A61M 37/00* (2006.01)

(52) U.S. Cl.
CPC .............. *A61N 1/042* (2013.01); *A61N 1/044* (2013.01); *A61N 1/0424* (2013.01); *A61N 1/0436* (2013.01); *A61N 1/327* (2013.01); *A61B 5/7239* (2013.01); *A61B 18/203* (2013.01); *A61B 2017/00761* (2013.01); *A61B 2017/00765* (2013.01); *A61B 2017/320004* (2013.01); *A61B 2018/00452* (2013.01); *A61B 2018/00642* (2013.01); *A61M 2037/0007* (2013.01); *A61N 1/328* (2013.01)

(58) Field of Classification Search
USPC ............ 600/547, 552, 556, 569; 604/20, 22; 606/131, 186, 204.35
See application file for complete search history.

(56) References Cited

U.S. PATENT DOCUMENTS

| | | |
|---|---|---|
| 3,551,554 A | 12/1970 | Herschler |
| 3,711,602 A | 1/1973 | Herschler |
| 3,711,606 A | 1/1973 | Herschler |
| 3,828,769 A | 8/1974 | Metler |
| 3,834,374 A | 9/1974 | Ensanian |
| 3,980,077 A | 9/1976 | Shaw, IV |
| 4,002,221 A | 1/1977 | Buchalter |
| 4,020,830 A | 5/1977 | Johnson |
| 4,027,664 A | 6/1977 | Heavner, Jr. et al. |
| 4,127,125 A | 11/1978 | Takemoto |
| 4,144,317 A | 3/1979 | Higuchi |
| 4,144,646 A | 3/1979 | Takemoto |
| 4,176,664 A | 12/1979 | Kalish |
| 4,249,531 A | 2/1981 | Heller |
| 4,274,419 A | 6/1981 | Tam et al. |
| 4,280,494 A | 7/1981 | Cosgrove |
| 4,309,989 A | 1/1982 | Fahim |
| 4,372,296 A | 2/1983 | Fahim |
| 4,457,748 A | 7/1984 | Lattin |
| 4,537,776 A | 8/1985 | Cooper |
| 4,538,612 A | 9/1985 | Patrick, Jr. |
| 4,557,943 A | 12/1985 | Rosler |
| 4,563,184 A | 1/1986 | Korol |
| 4,595,011 A | 6/1986 | Phillips |
| 4,605,670 A | 8/1986 | Saito et al. |
| 4,622,031 A | 11/1986 | Sibalis |
| 4,646,725 A | 3/1987 | Moasser |
| 4,657,543 A | 4/1987 | Langer et al. |
| 4,683,242 A | 7/1987 | Poser |
| 4,698,058 A | 10/1987 | Greenfeld |
| 4,702,732 A | 10/1987 | Powers |
| 4,732,153 A | 3/1988 | Phillips |
| 4,767,402 A | 8/1988 | Kost et al. |
| 4,769,022 A | 9/1988 | Chang et al. |
| 4,773,806 A | 9/1988 | Beaulieu |
| 4,775,361 A | 10/1988 | Jacques et al. |
| 4,778,457 A | 10/1988 | York |
| 4,786,277 A | 11/1988 | Power |
| 4,787,070 A | 11/1988 | Suzuki |
| 4,787,888 A | 11/1988 | Fox |
| 4,820,720 A | 4/1989 | Sanders |
| 4,821,733 A | 4/1989 | Peck |
| 4,821,740 A | 4/1989 | Tachibana et al. |
| 4,834,978 A | 5/1989 | Nuwayser |
| 4,855,298 A | 8/1989 | Yamada |
| 4,860,058 A | 8/1989 | Kobayashi |
| 4,863,970 A | 9/1989 | Patel |
| 4,866,050 A | 9/1989 | BenAmoz |
| 4,933,062 A | 6/1990 | Shaw |
| 4,948,587 A | 8/1990 | Kost |
| 4,953,552 A | 9/1990 | DeMarzo |
| 4,953,565 A | 9/1990 | Tachibana et al. |
| 4,970,145 A | 11/1990 | Bennetto et al. |
| 498,271 A | 1/1991 | Wilkins |
| 4,981,779 A | 1/1991 | Wagner |
| 4,986,271 A | 1/1991 | Wilkins |
| 5,001,051 A | 3/1991 | Miller |
| 5,003,987 A * | 4/1991 | Grinwald ..................... 600/547 |
| 5,006,342 A | 4/1991 | Cleary |
| 5,007,438 A | 4/1991 | Tachibana et al. |
| 5,008,110 A | 4/1991 | Benecke et al. |
| 5,016,615 A | 5/1991 | Driller |
| 5,019,034 A | 5/1991 | Weaver |
| 5,036,861 A | 8/1991 | Sembrowich |
| 5,050,604 A | 9/1991 | Reshef |
| 5,069,908 A | 12/1991 | Henley |
| 5,076,273 A | 12/1991 | Schoendorfer |
| 5,078,144 A | 1/1992 | Sekino |
| 5,082,786 A | 1/1992 | Nakamoto |
| 5,086,229 A | 2/1992 | Rosenthal |
| 5,115,805 A | 5/1992 | Bommannan et al. |
| 5,118,404 A | 6/1992 | Saito |
| 5,119,819 A | 6/1992 | Thomas |
| 5,120,544 A | 6/1992 | Henley |
| 5,134,057 A | 7/1992 | Kuypers |
| 5,135,753 A | 8/1992 | Baker |
| 5,139,023 A | 8/1992 | Stanley |
| 5,140,985 A | 8/1992 | Schroeder |
| 5,161,532 A | 11/1992 | Joseph |
| 5,165,407 A | 11/1992 | Wilson |
| 5,165,418 A | 11/1992 | Tankovich |
| 5,171,215 A | 12/1992 | Flanagan |
| 5,197,946 A | 3/1993 | Tachibana |
| 5,215,520 A | 6/1993 | Shroot |
| 5,215,887 A | 6/1993 | Saito |
| 5,230,344 A | 7/1993 | Ozdamar |
| 5,231,975 A | 8/1993 | Bommannan |
| 5,236,410 A | 8/1993 | Granov |
| 5,250,419 A | 10/1993 | Bernard |
| 5,267,985 A | 12/1993 | Shimada |
| 5,279,543 A | 1/1994 | Glikfeld |
| 5,282,785 A | 2/1994 | Shapland |
| 5,286,254 A | 2/1994 | Shapland |
| 5,315,998 A | 5/1994 | Tachibana |
| 5,323,769 A | 6/1994 | Bommannan |
| 5,330,756 A | 7/1994 | Steuart |
| 5,362,307 A | 11/1994 | Guy |
| 5,364,838 A | 11/1994 | Rubsamen |
| 5,386,837 A | 2/1995 | Sterzer |
| 5,401,237 A | 3/1995 | Tachibana |
| 5,405,366 A | 4/1995 | Fox |
| 5,405,614 A | 4/1995 | DAngelo |
| 5,413,550 A | 5/1995 | Castel |
| 5,415,629 A | 5/1995 | Henley |
| 5,421,816 A | 6/1995 | Lipkovker |

(56) References Cited

U.S. PATENT DOCUMENTS

| | | |
|---|---|---|
| 5,429,735 A | 7/1995 | Johnson |
| 5,443,080 A | 8/1995 | DAngelo |
| 5,445,611 A | 8/1995 | Eppstein |
| 5,458,140 A | 10/1995 | Eppstein |
| 5,470,582 A | 11/1995 | Supersaxo |
| 5,482,927 A | 1/1996 | Maniar et al. |
| 5,534,496 A | 7/1996 | Lee |
| 5,538,503 A | 7/1996 | Henley |
| 5,569,198 A | 10/1996 | Racchini |
| 5,573,778 A | 11/1996 | Therriault |
| 5,582,184 A | 12/1996 | Erickson |
| 5,582,586 A | 12/1996 | Tachibana et al. |
| 5,617,851 A | 4/1997 | Lipkovker |
| 5,618,275 A | 4/1997 | Bock |
| 5,626,554 A | 5/1997 | Ryaby |
| 5,633,234 A | 5/1997 | August |
| 5,636,632 A | 6/1997 | Bommannan |
| 5,643,252 A | 7/1997 | Waner et al. |
| 5,646,221 A | 7/1997 | Inagi |
| 5,655,539 A | 8/1997 | Wang |
| 5,656,016 A | 8/1997 | Ogden |
| 5,658,247 A | 8/1997 | Henley |
| 5,667,487 A | 9/1997 | Henley |
| 5,697,882 A * | 12/1997 | Eggers et al. ............... 604/114 |
| 5,722,397 A | 3/1998 | Eppstein |
| 5,730,714 A | 3/1998 | Guy |
| 5,735,273 A | 4/1998 | Kurnik |
| 5,746,217 A | 5/1998 | Erickson |
| 5,771,890 A | 6/1998 | Tamada |
| 5,782,754 A | 7/1998 | Korf et al. |
| 5,814,599 A | 9/1998 | Mitragotri |
| 5,820,570 A | 10/1998 | Erickson |
| 5,827,183 A | 10/1998 | Kurnik |
| 5,833,647 A | 11/1998 | Edwards |
| 5,851,438 A | 12/1998 | Chan |
| 5,885,211 A | 3/1999 | Eppstein |
| 5,895,362 A | 4/1999 | Elstrom et al. |
| 5,902,603 A | 5/1999 | Chen |
| 5,906,830 A | 5/1999 | Farinas |
| 5,913,833 A | 6/1999 | Elstrom et al. |
| 5,919,835 A | 7/1999 | Domb et al. |
| 5,947,921 A | 9/1999 | Johnson et al. |
| 5,961,451 A | 10/1999 | Reber |
| 5,989,409 A | 11/1999 | Kurnik et al. |
| 6,002,961 A | 12/1999 | Mitragotri |
| 6,009,343 A | 12/1999 | Shain et al. |
| 6,018,678 A | 1/2000 | Mitragotri |
| 6,032,060 A | 2/2000 | Carim |
| 6,041,252 A | 3/2000 | Walker |
| 6,042,253 A | 3/2000 | Fant, Jr. |
| 6,056,738 A | 5/2000 | Marchitto et al. |
| 6,113,561 A | 9/2000 | Augustine |
| 6,126,619 A | 10/2000 | Peterson et al. |
| 6,139,718 A | 10/2000 | Kurnik et al. |
| 6,141,582 A | 10/2000 | Mori et al. |
| 6,148,232 A * | 11/2000 | Avrahami ............... 604/20 |
| 6,190,315 B1 | 2/2001 | Kost |
| 6,234,990 B1 | 5/2001 | Rowe et al. |
| 6,251,083 B1 | 6/2001 | Yum |
| 6,251,100 B1 | 6/2001 | Flock et al. |
| 6,283,926 B1 | 9/2001 | Cunningham |
| 6,299,578 B1 | 10/2001 | Kurnik et al. |
| 6,309,351 B1 | 10/2001 | Kurnik |
| 6,309,353 B1 | 10/2001 | Cheng et al. |
| 6,315,722 B1 | 11/2001 | Yaegashi |
| 6,321,109 B2 | 11/2001 | Ben-Haim et al. |
| 6,398,753 B2 | 6/2002 | McDaniel |
| 6,463,314 B1 | 10/2002 | Haruna |
| 6,468,229 B1 | 10/2002 | Grace |
| 6,482,604 B2 | 11/2002 | Kwon |
| 6,487,447 B1 | 11/2002 | Weimann |
| 6,491,657 B2 | 12/2002 | Rowe |
| 6,503,198 B1 | 1/2003 | Aronowtiz |
| 6,535,753 B1 | 3/2003 | Raskas |
| 6,540,675 B2 | 4/2003 | Aceti |
| 6,546,378 B1 | 4/2003 | Cook |
| 6,887,239 B2 | 5/2005 | Elstrom et al. |
| 7,133,717 B2 * | 11/2006 | Coston et al. ............... 604/20 |
| 2003/0100846 A1 | 5/2003 | Custer |
| 2003/0204329 A1 | 10/2003 | Marchitto et al. |
| 2004/0039418 A1 | 2/2004 | Elstrom |
| 2004/0059282 A1 * | 3/2004 | Flock et al. ............... 604/20 |
| 2004/0171980 A1 * | 9/2004 | Mitragotri et al. ............ 604/20 |
| 2004/0236268 A1 | 11/2004 | Mitragotri et al. |
| 2006/0094945 A1 | 5/2006 | Barman et al. |
| 2006/0100567 A1 | 5/2006 | Marchitto et al. |
| 2007/0135729 A1 * | 6/2007 | Ollmar et al. ............... 600/547 |

FOREIGN PATENT DOCUMENTS

| | | |
|---|---|---|
| CA | 2196746 | 8/1999 |
| DE | 2756460 | 6/1979 |
| EP | 0 043 738 | 1/1982 |
| EP | 0 246 341 | 11/1987 |
| EP | 0 495 531 | 7/1992 |
| EP | 0 513 789 | 11/1992 |
| EP | 0 612 525 | 8/1994 |
| EP | 0 649 628 | 4/1995 |
| EP | 0 736 305 | 10/1996 |
| GB | 1577551 | 6/1979 |
| GB | 1 577 551 | 10/1980 |
| JP | 5995060 | 5/1984 |
| JP | 6213937 | 6/1987 |
| JP | 2224752 | 9/1990 |
| JP | 3 170 172 | 7/1991 |
| RU | 445433 | 11/1974 |
| RU | 556805 | 6/1977 |
| RU | 591186 | 1/1978 |
| RU | 506421 | 2/1978 |
| RU | 910157 | 3/1982 |
| WO | WO 90/01971 | 8/1990 |
| WO | WO 90/15568 | 12/1990 |
| WO | WO 93/05096 | 3/1993 |
| WO | WO 95/02357 | 1/1995 |
| WO | WO 96/00110 | 1/1996 |
| WO | WO 97/02811 | 1/1997 |
| WO | WO 97/04832 | 2/1997 |
| WO | 9707734 | 3/1997 |
| WO | 9713548 | 4/1997 |
| WO | WO 97/18851 | 5/1997 |
| WO | 9730749 | 8/1997 |
| WO | WO 98/00194 | 1/1998 |
| WO | WO 98/17184 | 4/1998 |
| WO | 9820331 | 5/1998 |
| WO | WO 98/28037 | 7/1998 |
| WO | WO 99/34857 | 7/1999 |
| WO | WO 99/34858 | 7/1999 |
| WO | 9939763 | 8/1999 |
| WO | WO 00/04821 | 2/2000 |
| WO | 0035357 | 6/2000 |
| WO | WO 00/35351 | 6/2000 |
| WO | WO 00/35357 | 6/2000 |
| WO | WO 01/03638 | 1/2001 |
| WO | WO 00127473 | 1/2001 |
| WO | WO 01/70330 | 9/2001 |
| WO | WO 02/011813 | 2/2002 |
| WO | WO 03/039620 | 5/2003 |
| WO | WO 03/090366 | 10/2003 |
| WO | WO 2004/019777 | 3/2004 |
| WO | WO 2006/045149 | 5/2006 |
| WO | WO 2006/054150 | 5/2006 |

OTHER PUBLICATIONS

Albin, et al., "Theoretical and experimental studies of glucose sensitive membranes", *Journal of Controlled Release*, 6 (1):267-291, (1987).

Allcock, et al., "Activity of urea amidohydrolase immobilized within poly[di(methoxyethoxyethoxy)phosphazeriel hydrogels", *Biomaterials*, 15(7):502-6 (1994).

Apfel, "Possibility of microcavitation from diagnostic ultrasound"*IEEE Trans. Ultrason Ferroelectrics Freq. Control UFFC*, 33:139-142 (1986).

(56) References Cited

OTHER PUBLICATIONS

Asakura, et al., "Immobilization of glucose oxidase on nonwoven fabrics with bombyx mod silk fibroin gel",*J. Appl. Pol. Sci.*, 4(1):49-53 (1992).
Aungst, et al., "Contributions of drug solubilization, partitioning, barrier disruption, and solvent permeation to the enhancement of skin permeation of various compounds with fatty acids and amines", *Pharm Res.*, 7(7):712-8 (1990).
Barry, et al., "Mode of Action of Penetration Enhancers in human skin", *J. Control. Rel.*, 6:85-97 (1987).
Bhat, et al., "Optimization of delivery of bethamethasone-dipropionate from skin preparation", *Indian Drugs*, 32:211-214 (1995).
Blackshear, "Implantable drug-delivery systems", *Scientific America*, 241(56):66-73 (1979).
Bommer et al., "*Subcutaneous erythropoietin*", *Lancet*, 2(8607):406 (1988).
Boucaud, et al., "Clinical, histologic, and electron microscopy study of skin exposed to low-frequency ultrasound", *Anat Rec.*, 264(1):114-9 (2001).
Boucaud, et al., "In vitro study of low-frequency ultrasound-enhanced transdermal transport of fentanyl and caffeine across human and hairless rat skin", *Int J Pharm.*, 228(1-2):69-77 (2001).
Burnette, "Iontophoresis", in Transdermal Drug Delivery Development Issues and Research Initiatives p. 247-291 (Hadgraft and Guy, Eds. Marcel Dekker, 1989).
Burton, et al., "Metabolism and transport of peptide across intestinal mucosa" 14 Proceed. Intern. Symp. Control. Rel. Bioact. Mater 6 (Controlled Release Society, Inc. 1987).
Camel, "Ultrasound" in Percutaneous Penetration Enhancers p. 369-382 (Eric W. Smith, et al. eds.1995).
Chlup, et al., "Function and accuracy of glucose sensors beyond their stated expiry date", *Diabetes Technology & Therapeutics*, 8(4):495-504 (2005).
Chuang, et al, "Ultrasonic Pretreatment Enables Continuous Transdermal Glucose Monitoring", Presented at the 4th Annual Diabetes Technology Meeting Held Oct. 28-30, 2004, (Philadelphia, PA).
Cleary, "Transdermal Controlled Release Systems," in Medical Applications of Controlled Release 203-251 (Langer and Wise eds. CRC Press 1984).
Cleg and Vaz, " Translational diffusion of proteins and lipids in artificial lipid bilayer membranes, A comparison of experiment with theory", in Progress in Protein-Lipid interactions Watts, ed. Chapter 5:173.339 (Elsevier, NY 1985).
Davis, et al, "Characterization of recombinant human erythropoietin produced in Chinese hamster ovary cells", *Biochemistry*, 26(9):2633-8 (1987).
D'Emanuele, et al., "An investigation of the effects of ultrasound on degradable polyanhydride matrices"*Macromols.*, 25:511-515 (1992).
Domb, et al., "Polyanhydrides-Synthesis and Characterization," 107 Advances in Polymer Science: 93-141 (1993).
Ebert, et al., "Transbuccal Absorption of Diclofenac Sodium in a Dog Model," Controlled Release Technology Pharmaceutical Application 310-321 (Lee, et al. Editors, American Chemical Society, 1987).
Eggerth, et al; "Evaluation of Hamster Cheek Pouch as a Model for Buccal Absorption,"*Proceed. Intern. Symp. Rel. Bioact. Mater.* 14:180-181 (Controlled Release Society, Inc. 1987).
Elias, "The Microscopic Structure of the Epidermis and its Derivatives," Percutaneous Absorption: Mechanisms—Methodology—Drug Delivery 1-12 (1989).
Eppstein, et al., "Alternative Delivery Systems for Peptides and Proteins as Drugs,"*Crit Rev Ther. Drug Carrier Syst.*, 5:99-139 (1988).
Eppstein, Applications of Liposome Formulations for Antimicrobial/Antiviral Therapy, In: Liposomes as Drug Carriers, Gregoriadis G. eds, pp. 311-323, John Wiley & Sons, Chichester, 1988.
Eppstein, et al; "Medical Utility of Interferons: Approaches to Increasing Therapeutic Efficacy", Pharmacy International 7:195-199 (1986).
Flynn, "Mechanism of Percutaneous Absorption from Physicochemical Evidence," in: Bronaugh R. Maibach Hi. Eds. Percutaneous Absorption: Mechanisms—Methodology—Drug Delivery, New York, NY, Marcel Dekker, pp. 27-51 (1989).
Gaertner, "Frequency dependence of Ultrasonic Cavitation,"*J. Acoust. Soc, Am.* 26:977-980 (1954).
Ghanem, et al; "The effects of ethanol on the transport of lipophilic and polar permeants across hairless mouse skin: Methods/validation of a novel approach,"*Int. J. Pharm.*, 78:137-156 (1992).
Grups and Frohmueller, "Cyclic Interferon Gamma Treatment of Patients with Metastatic Renal Carcinoma,"*Br. J. Urol.*, 64(3):218-220 (1989).
Heller, et al., "Controlled Drug Release by Polymer Dissolution II Enzyme-Mediated Delivery Device,"*J. Of Pharm. Sci.*, vol. 68(7):919-921 (1979).
Hill-West, et al., "Inhibition of thrombosis and intimal thickening by in situ photopolymerization of thin hydrogel barriers", *Proc Natl Acad Sci U.S.A.*, 91:5967-71 (1994).
Johnson, et al., "Synergistic effects of chemical enhancers and therapeutic ultrasound on transdermal drug delivery,"*J. Pharm. Sci.*, 85:670-679 (1996).
Junginger, et al., "Visualization of Drug Transportation Across Human Skin and the Influence of Penetration Enhancers," in: Drug Permeation Enhancement Hsieh, D.S., Editors, Marcel Dekker, Inc. New.York (1994) pp:59-89.
Kamath, et al; "Biodegradable hydrogels in Drug Delivery,"*Adv. Drug Delivery Rev.*, 11:59-84 (1993).
Kasting, et al; "Prodrugs for Dermal Delivery: Solubility, molecular Size, and Functional Group Effects,"in: Prodrugs: Topical and Ocular Delivery Sloan, ed. (Marcel Dekker, NY 1992) pp:117-161.
Keith and Snipes, "Polymeric carriers for Active Agents," in: Transdermal and Related Drug Delivery Systems pp. 223-279 (D. A. Jones ed. 1984).
Klonoff, "A review of continuous glucose monitoring technology", *Diabetes Technology & Therapeutics*, 7(5):770-775.
Kost and Langer, "Ultrasound-Mediated Transdermal Drug Delivery," in: Topical Drug Bioavailability Bioequivalence and Penetration (Maibach, H. I., Shah, V. P., Editors, Plenum Press, New York) 91-104 (1993).
Kost, et al; "Ultrasound Effect on Transdermal Drug Delivery," Proceeding of the 13$^{th}$ International Symposium on Controlled Release of Bioactive Materials, Norfolk, VA, 1986, pp. 177-178.
Kost, et al., "Glucose-Sensitive Membranes containing Glucose Oxidase: Activity, Swelling, and Permeability Studies,"*J. Of Biomed. Mat. Res.*, 19: 1117-1133 (1985).
Krall, "World Book of Diabetes in Practice," vol. 3, pp. 2-7 (Elsvier, 1988).
Langer, et al., "Chemical and Physical Structure of Polymers as Carriers for Controlled Release of Bioactive Agents: A Review,"*J. of Macromol. Sci., Reviews on Macromolecular Chemistry and Physics*, C23(1):61-126 (1983).
Lee & Rashi, "Nasal Peptide and Protein Absorption Promoters: Aminopeptidase Inhibition as a Predictor of Absorption Enhancement Potency of Bile Salts,"*Proc. Intern. Symp. Control. Rel. Bioact. Mater.*, 14:53-54 (1987).
Lee, et al., "Protease Inhibition as an Additional Mechanism for the Nasal Absorption Enhancement Effect of Sodium Taurodihydrofusidate,"*Proceed. Intern, Symp. Control. Rel. Bioact. Mater.*, 14, 55-56 (1987).
Lesho, at al., "A Photopatterned Glucose Responsive Hydrogel for Use in a Conductimetric Sensor," lin: Biomaterials for Drug and Cell Delivery, Materials Research Society Symposium Proceedings, vol. 331, pp. 193-198 (1994).
Levy, et al., "Effect of ultrasound on transdermal drug delivery to rats and guinea pigs", *J. Clin. Invest.*, 83:2074-2078 (1989).
Liu, at al., "Experimental Approach to Elucidate the Mechanism of Ultrasound-enhanced Polymer Erosion and Release of Incorporated Substances,"*Macromolecules*, 25:123-128 (1992).

(56) References Cited

OTHER PUBLICATIONS

Liu, et al., "Cotransport of Estradiol and Ethanol Through Human Skin in Vitro: Understanding the Permeant/ Enhancer Flux Relationship,"*Pharm. Res.*, 8:938-944 (1991).
Machluf and Kost, "Ultrasonically Enhanced transdermal drug delivery, Experimental approaches to elucidate the mechanism,"*J. Biomater. Sci. Polymer Edn*, 5:147-156 (1993).
Mak, et al., "Oleic Acid Concentration and Effect in Human Stratum Corneum: Non-Invasive Determination by Attenuated Total Reflectance Infrared Spectroscopy in Vivo", *J. Control Rel.*, 12:67-75 (1990).
Mezei, "Liposomes as a Skin Drug Delivery System," Topics in Pharmaceutical Sciences pp. 345-357 (1985).
Mitragotri, et al, "A Mechanistic Study of Ultrasonically-Enhanced Transdermal Drug Delivery,"*J. Pharm. Sci.*, 84(6):697-706 (1995).
Mitragotri, et al., "Ultrasound-Mediated Transdermal Protein Delivery, "*Science*, 269:850-853 (1995).
Mitragotri, et al., "Sonophoresis: Enhanced Transdermal Drug Delivery by Application of Ultrasound,"*Encyclopedia of Pharmaceutical Technology*, 14:103-122 (1996).
Mitragotri, et al., "Synergistic Effect of Low-frequency Ultrasound and Sodium Lauryl Sulfate on Transdermal Transport,"*J. Pharm. Sci*, 89(7):892-900 (2000).
Mitragotri, "Synergistic Effect of Enhancers for Transdermal Drug Delivery,"*Pharm Res.*, 17(11):1354-1359 (2000).
Mitragotri & Kost, "Transdermal Delivery of Heparin and Low-Molecular Weight heparin Using Low-frequency Ultrasound,"*Pharm. Res.*, 18(8):1151-1156 (2001).
Miyakazi, et al, "Controlled Drug Release by Ultrasound Irradiation,"*Chemical & Pharmaceutical Bulletin*, 33(1):428431 (1985).
Monti, et al., "Comparison of the effect of ultrasound of Chemical enhancers on transdermal permeation of caffeine and morphine through hairless mouse skin in vitro," International J. Pharmaceuticals, vol. 229, Nos. 1-2, pp. 131-137 (Oct. 2001).
Morimoto, et al., "Prediction of Skin Permeability of Drugs: Comparison of Human and Hairless Rat Skin,"*J. Pharm. Pharmacol.* 44: 634-639 (1991).
Murav'Ev, et al., "Mechanism of the Release of Pharmaceutical Substances from Ointment bases by ultrasound," Chemical Abstacts, vol. 84, No. 4 ,p. 333, Abstract No. 22054g (Jan. 26, 1976).
Nagai, et al., "Buccal/Gingival Drug Delivery Systems,"*J. Control. Rel.*, 6:353-360 (1987).
Newman, et al., "Hydrocortisone Phonophoresis,"*J. Am. Pod. Med. Assoc.* 82:432-435 (1992).
Olanoff & Gibson, "Method to Enhance Intranasal Peptide Delivery," Controlled Release Technology Pharmaceutical Application (Lee, et al, Editors, American Chemical Society) 301-309 (1987).
Ongpipattanankul, et al., "Evidence that Oleic Add Exists in a Separate Phase Within Stratum Comeum Lipids,"*Pharm. Res.*, 8:350-354 (1991).
Otsuka, et al., "Use of Ultrasonic Waves in Pharmacy — I & II Degradation of Polymers,"*Chemical Abstracts*, vol. 69, No. 20, pp. 7513, Abstract No. 80161r & No. 80162 (Nov. 11, 1968).
Perkin, et al., "Atopic manifestations in the acquired immune deficiency syndrome: response to recombinant interferon gamma", Br. Med. J., 294:1185-1186 (1987).
Pishko, et al., "Amperometric Glucose Microelectrodes Prepared through Immobilization of Glucose Oxidase in Redox Hydrogels", *Anal. Chem.*, 63:2268-2272 (1991).

Potts & Guy, "Predicting Skin Permeability", *Pharm. Res.*, 9:663-669 (1992).
Prausnitz, et al., "Electroporation of mammalian skin: A mechanism to enhance transdermal drug delivery", *Proc. Natl. Acad. Sci.* USA, 90:10504-10508 (1993).
Quillen, "Phonophoresis: A Review of the Literature and Technique", *Athl. Train.*, 15:109-110 (1980).
Remington's Pharmaceutical Sciences, Chapter 19—Disperse Systems pp. 267-272 Chapter 87—Medicated Appliances pp. 1600-1606, 1614 Chapter 91—Sustained-Release Drug Delivery Systems pp. 1690-1693, Mack Publishing Co.
Robinson & Lee, "Influence of Drug Properties on Design", in:Controlled Drug Delivery, Mercer Dekker, Inc. n. Y. (1987) pp. 42-43.
Rosell, et al., 'Skin Impedance From 1 Hz to 1 MHz', *IEEE Trans. Biomed. Eng.*, 35:649-651 (1988).
Schreier & Bouwstra, "liposome and noisomes as topical drug carriers: dermal and transdermal drug delivery", J. Control. Rel, 30:1-15 (1994).
Skauen, et al., "Phonophoresis", *Int. J, Pharm.* 20:235-245 (1984).
Tamada, et al., "Correlation of blood glucose with iontophoretic glucose flux in human subjects for glucose monitoring", *Proceed. Intern. Symp. Control. Rel. Bioact. Mater.* 22:129-130 (1995).
Tang, et al., "Theoretical description of transdermal transport of hydrophilic permeants: application to low-frequency sonophoresis"*J Pharm Sci*, 90(5):545-68 (2001).
Tezel, et al., "Synergistic effect of low-frequency ultrasound and surfactants on skin permeability", *J Pharm Sci.*, 91(1):91-100 (2002).
Tierney, et al., "The GlucoWatch biographer: a frequent automatic and noninvasive glucose monitor", *Annals of Medicine*, 32(9):632-641 (2000).
Tocanne, et al., "Lipid lateral diffusion and membrane organization", *FEBBS Lett.*, 257:10-16 (1989).
Tyle & Agrawala, "Drug Delivery by Phonophoresis", *Pharm. Res.*, 6:355-361 (1989).
Veillard, et al., "Buccal Controlled Delivery of Peptides"*Proceed Intern. Symp. Control. Rel. Bioact. Matter.* , 14:22 (1987).
Walker & Hadgraft, "Oleic acid—a membrane 'fluidiser' or fluid within the membrane", *Int. J. Pharm.*, 71:R1-R4 (1991).
Walmsley, "Applications of Ultrasound in Dentistry", *Ultrasound in Med. And Biol.*, 14:7-14 (1988).
Walters, "Penetration Enhancers and Their Use in Transdermal Therapeutic Systems", in: Transdermal Drug Delivery: Developmental Issues and Research Initiatives, 197-246 (Hadgraft. J., Guy, R.H., Editors, Marcel Dekker, 1989).
Wester & Mailbach, "Animal Models for Percutaneous Absorption", Topical Drug Bioavailability Bioequivalence and Penetration (Shah and Maibach, Editors, Plenum Press, New York) 333-349, (1993).
Wheatley, et al., "Use of Ussing Chamber for Investigation of Drug Delivery Across Viable Nasal Tissue Membranes", *Proceed. Intern. Symp. Control. Rel. Bioact. Mater.* 14:26-27 (1987).
Williams, et al., "On the non-Gaussian distribution of human skin permeabilities", *Int. J. Pharm.*, 86:6977 (1992).
Wilschut, et al., "Estimating Skin Permeation, The Validation of Five Mathematical Skin Permeation Models", *Chenzosphere*, 30:1275-1296 (1995).
Egorov, et al. "Use of the Variants of the Pharmacophysical Influence in Ophthalmology," Vestn Oftalmol., 108(2):52-4 (1992).

\* cited by examiner

Disposable abrasive tip

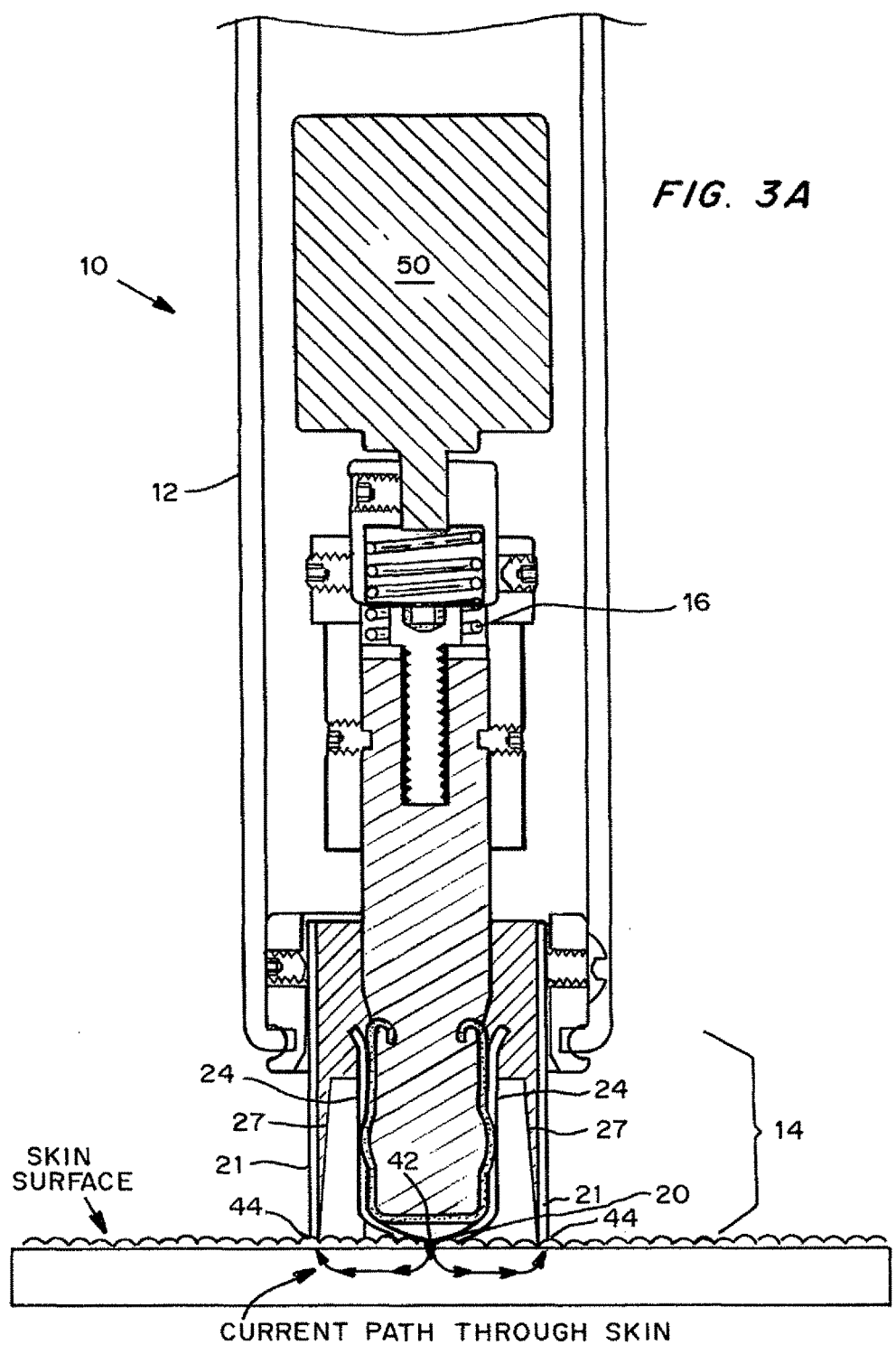

SKIN PERMEATION DEVICE FOR ANALYTE SENSING OR TRANSDERMAL DRUG DELIVERY

CROSS-REFERENCE TO RELATED APPLICATION

This application is a continuation of pending application U.S. application Ser. No. 12/110,034 entitled "Skin Permeation Device for Analyte Sensing or Transdermal Drug Delivery" by Han Chuang, Juan P. Eslava, James P. Hurley, Debashis Ghosh, Keith Krystyniak and Scott C. Kellogg, filed Apr. 25, 2008, which claims priority to U.S. Ser. No. 60/914,552, entitled "Device for Permeabilizing Skin for Analyte Sensing or Transdermal Drug Delivery", filed Apr. 27, 2007, the disclosure of which is incorporated by reference.

FIELD OF THE INVENTION

The present invention is directed to the field of devices and methods for transdermal analyte sensing or drug delivery.

BACKGROUND OF THE INVENTION

In general, permeation of drugs through the skin occurs at a very slow rate, if at all. The primary rate limiting step in this process is the passage of compounds through the outermost layer of skin, called the stratum corneum. The stratum corneum is a thin layer of dead cells that acts as an impermeable layer to matter on either side of this layer. The stratum corneum primarily provides the skin's barrier function. It has long been recognized that loss or alteration of the stratum corneum results in increased permeability to many substances; materials can more easily diffuse into or out of the skin. The barrier function of the skin presents a very significant problem to pharmaceutical manufacturers interested in transdermal administration of drugs or in cutaneous collection of bodily fluids.

Transmission and reception of electrical signals and biological materials through human skin is also hindered by the stratum corneum. For example, signal fidelity of bioelectrical potentials and currents measured through skin are degraded by the high impedance of the stratum corneum. Accordingly, the high impedance presents a problem to receiving through the skin the ideal transmission and measurement of bioelectrical signals from human cells, organs, and tissues.

Removal of the stratum corneum reduces the high impedance of the skin and allows better transmission and reception of electrical signals or biological species into and from human tissues. It has also been demonstrated that electromagnetic energy induced alterations of the stratum corneum result in increased permeability to substances (see e.g. U.S. Pat. No. 6,315,722 to Yaegashi, U.S. Pat. No. 6,251,100 to Flock et al., U.S. Pat. No. 6,056,738 to Marchitto et al., and U.S. Pat. No. 5,643,252 to Waner et al.). Alternatively, compounds commonly referred to as "permeation enhancers" can be used, with some success, to penetrate the stratum corneum. Traditional approaches require the abrasion of skin with sand paper and brushes, the stripping of skin with tape and toxic chemicals, the removal of stratum corneum by laser or thermal ablation, or the puncturing of skin with needles. Preparation of skin by these methods may be highly variable, hazardous, painful to the subject, and are generally inconvenient.

Conventional approaches for skin preparation for drug delivery or extraction of analytes through the skin require external feedback mechanism to control the extent of skin preparation. In practice, an electrically conductive coupling medium, a return electrode and/or a hydrogel patch are generally needed to enable the feedback mechanism for controlled skin preparation (see e.g. U.S. Publication No. 20060100567 to Marchitto et al. and U.S. Publication No. 20030204329 to Marchitto et al.). The reliability of such devices and systems can be questionable since the return electrode can provide accurate feedback only when located on a skin site which has sufficient electrical conductivity. Unfortunately, conductivity of the skin varies by a variety of conditions, such as age, location, sun exposure, use of lotions, moisture level, and ambient conditions, etc.

Therefore, an improved system for reducing the high impedance of the skin is needed.

It is an object of the invention to provide an improved system for reducing the high impedance of the skin.

It is a further object of the invention to provide an improved method for measuring the impedance of the skin.

It is yet a further object to provide an improved transdermal drug delivery and/or analyte sensing system.

SUMMARY OF THE INVENTION

Devices, systems, kits and methods for increasing the skin's permeability are described herein. They may be used for transdeimal drug delivery and/or analyte extraction and measurement. The controlled abrasion device contains (i) a hand piece, (ii) an abrasive tip, (iii) a feedback control mechanism, (iv) two or more electrodes, and (v) an electrical motor. Preferably the feedback control mechanism is an internal feedback control. In this embodiment, the abrasive tip contains two electrodes, i.e. both the source electrode and the return electrode. In another embodiment, the feedback control mechanism is an external feedback control. In the preferred embodiment for external feedback control, the device contains a co-axial or concentric arrangement of the two electrodes. In this embodiment, the abrasive tip contains the source electrode and the return electrode is located at the proximal end of the hand piece. The abrasive tip can be made of any material with a surface that can abrade skin. The material can be conductive or non-conductive. In the preferred embodiment, the material is a conductive material. Optionally, the abrasive tip is wetted with a wetting fluid prior to application on the skin. The controlled abrasion device may be provided in a kit, where the kit contains the device, one or more abrasive tips, and, optionally, a wetting fluid. In one embodiment, the abrasive tip is moistened with the wetting fluid and sealed in a container to retain the wetting fluid in the tip. In another embodiment, the wetting fluid is supplied in a separate container or in a material, such as a prepackaged wipe. The method for increasing the skin's permeability includes applying the controlled abrasion device to a portion of the skin's surface for a short period of time, such as for up to 30 seconds. The desired level of skin impedance or conductance, and thus the resulting permeability of the treated site, can be set at a predetermined value.

Alternatively, the level of skin impedance or conductance can be selected based on the desired level of skin integrity, the subject's sensation of discomfort, or the duration of the application. The device contains a feedback circuit as part of the feedback control mechanism, which uses an appropriate algorithm or signal processing based on the conductivity information to determine when the desired level of skin permeability has been reached. Once the desired level of permeability has been reached, the abrasion device is removed and either a drug delivery composition or device or an analyte sensor is applied to the treated site.

BRIEF DESCRIPTION OF THE DRAWINGS

FIG. 2A contains a front view and an exploded view of the abrasive tip shown relative to an abrasion device, and FIG. 2B is a side view of the abrasive tip, shown in contact with the skin surface.

FIGS. 3A-D are illustrations of a controlled abrasion device using external feedback control mechanism. FIG. 3A is a cross-sectional view of the controlled abrasion device, which illustrates the current path through the skin and into the device. FIGS. 3B and 3C are bottom plan views of the proximal end of the controlled abrasion device that illustrate a co-axial or concentric arrangement of the two electrodes. FIG. 3B illustrates an abrasive tip that also serves as the source electrode. FIG. 3C illustrates an abrasive tip in which a conductive element is inserted therein, where the conductive element serves as the source electrode. FIG. 3D is a cross-sectional view of the proximal end of a disposable abrasive tip, which illustrates the contact of the source electrode with a spring that provides a conductive path from the abrasive tip to the motor shaft.

DETAILED DESCRIPTION OF THE INVENTION

The devices, systems, kits and methods described herein provide a convenient, rapid, economic, and minimally invasive system and method for increasing the skin's permeability. These devices, systems, kits and methods may be used for transdermal drug delivery and/or analyte measurement.

I. Controlled Abrasion Device

Figure 1:
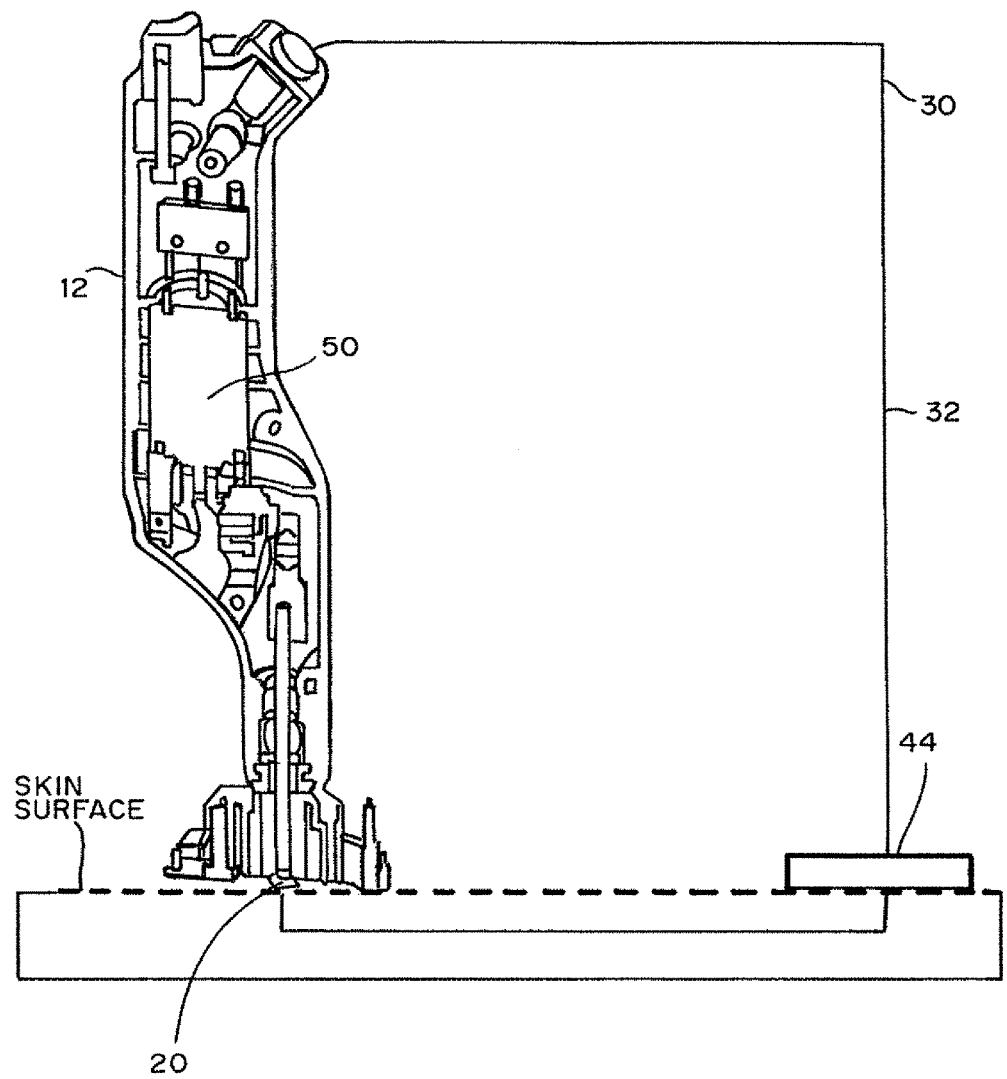
FIG. 1 is shows an exemplary controlled abrasion device using an external feedback control mechanism.

A controlled abrasion device (10) is illustrated in FIG. 1. The device contains (i) a hand piece (12), (ii) an abrasive tip (20), (iii) a feedback control mechanism (30), (iv) two or more electrodes (40), and (v) an electrical motor (50). The devices may contain additional controls and/or a user interface.

Figure 2A:
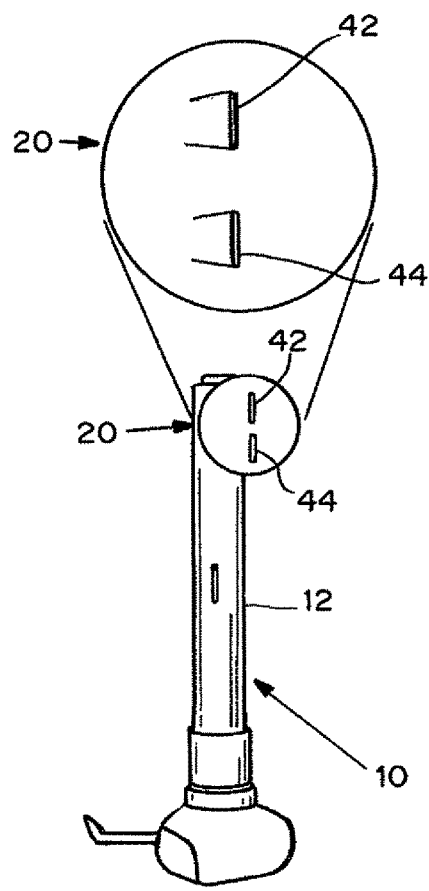
FIGS. 2A and 2B are illustrations of an abrasive tip containing two electrodes for an internal feedback control.

The devices illustrated in FIGS. 1 and 3A-D have external feedback control mechanisms. Preferably the feedback control mechanism is an internal feedback control mechanism. An exemplary controlled abrasion device with an internal feedback control mechanism is illustrated in FIG. 2A.

a. Abrasive Tip

The abrasive tip (20) may be reusable or disposable. If the abrasive tip is reusable, it is designed to be cleaned between uses and reused. In a preferred embodiment, the abrasive tip is disposable.

A disposable abrasive tip is attachable to and removable from the proximal end of the hand piece by any suitable connecting means.

Figure 3B:
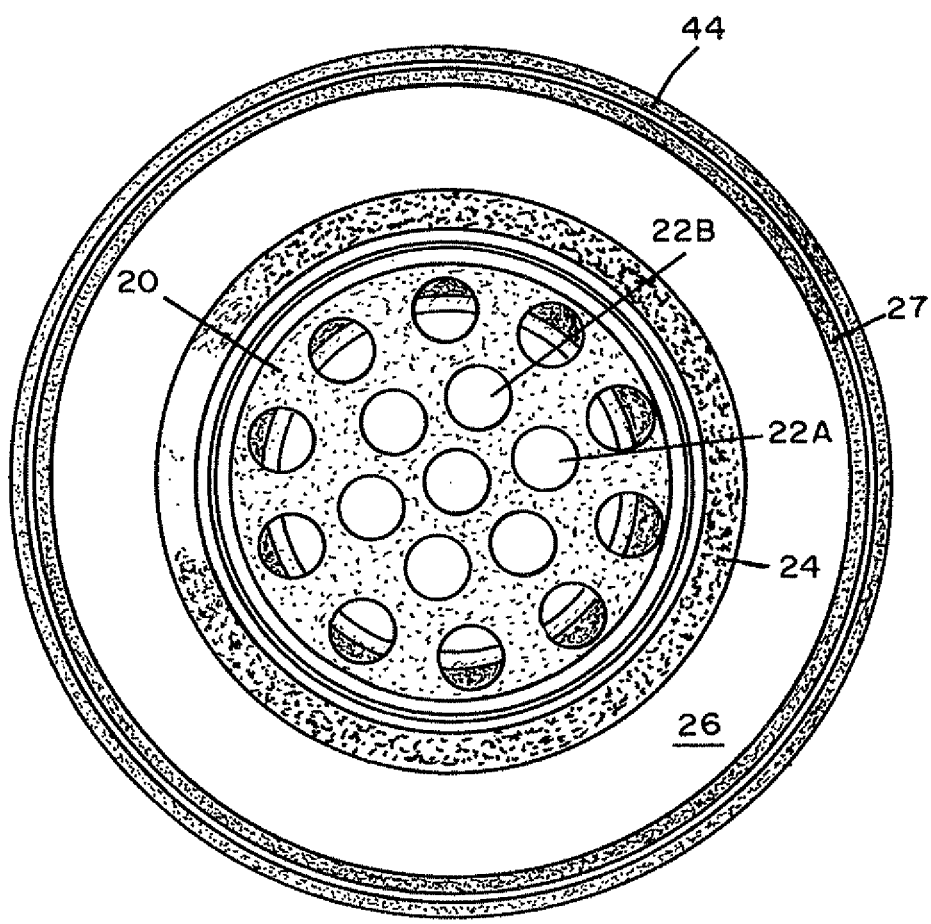
Figure 3C:
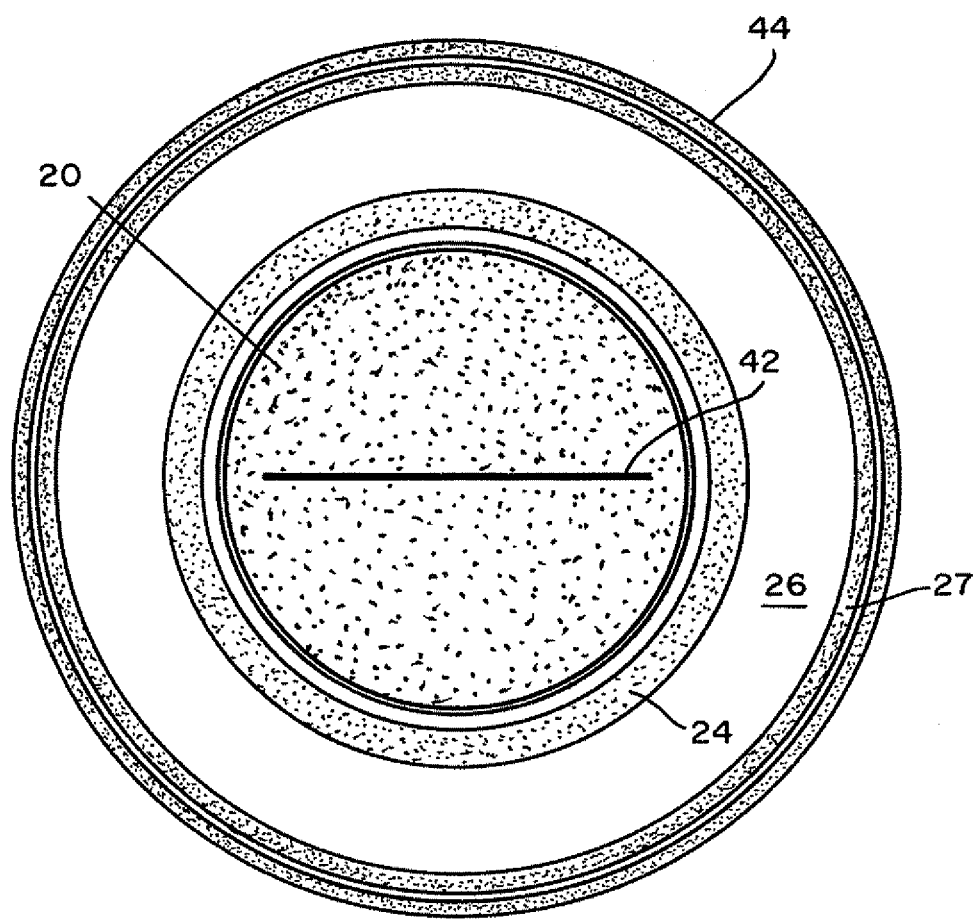
Figure 3D:
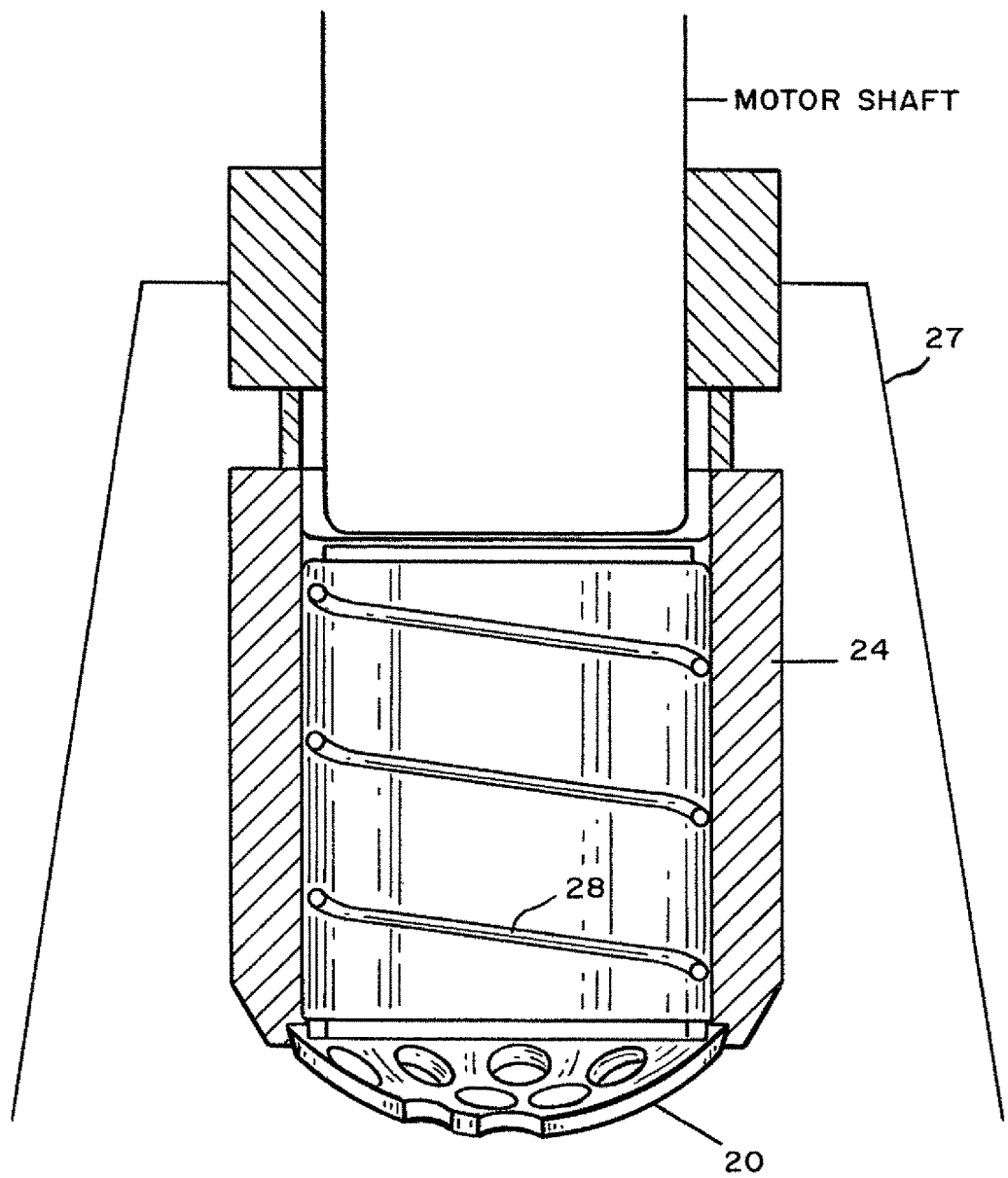

A preferred embodiment of the disposable abrasive tip is illustrated in FIGS. 3A and 3D. In a preferred embodiment, the disposable abrasive tip is attached to a tube (24), preferably a plastic tube. The tube (24) is inserted into a central void in a plastic cup or cone (27), where the central void is shaped to receive the tube while allowing the tip to move when the device is turned on (see FIG. 3D). The cup or cone (24) is designed to prevent fluids from contacting the hand piece (12), thereby minimizing or eliminating cleaning of the hand piece after use. In the preferred embodiment, the opening (25) of the cup or cone (24) fits inside the outer wall (21) of the proximal end (14) of the hand piece (12) (see FIG. 3D). In the preferred embodiment the outer wall (21) contains a conductive material that serves as the return electrode (44).

i. Materials

The abrasive tip can be made of any material with a surface that can abrade skin, such as sand paper, rough textiles, such as dermal grade fabrics that are used in cosmetic microdermabrasion, typically made from 100% medical grade nylon and have a plurality of coatings and finishes, wire brushes, carbon fibers, or microneedles. The material can be conductive or non-conductive. For example, white aluminum oxide, a non-conductive material, is readily available at low cost in medical grade. This material is able to withstand elevated temperatures, such as those typically present in any vitrification process that may be necessary for high volume binding/fabrication to produce the abrasive tip. In some embodiments, a softer material than aluminum oxide is preferred so that the material is less irritating to the skin than aluminum oxide. Polymeric beads may be used as the abrasive material in place of aluminum oxide. Generally the polymeric beads provide a softer, less irritating material than aluminum oxide. Material preference is based on the particular individual to be treated and the purpose of the treatment. Thus for different individuals, different materials may be substituted for the above-listed materials.

With proper engineering designs, it is possible that conductive materials can also be used as the abrasive material in the abrasive tip. Suitable conductive materials include, but are not limited to, metals, carbon, conductive polymers and conductive elastomers.

In a preferred embodiment, the material is a conductive material, preferably a metal, most preferably stainless steel sheet metal, with multiple holes or perforations (22A and B). An example of this embodiment is illustrated in FIG. 3B. The abrasive tip may be formed by punching the material to form a disc with a diameter that corresponds with the area of the skin to be abraded. The disc then shaped into a dome and attached to a tube (24), preferably a plastic tube.

ii. Dimensions

The abrasive tip can have any suitable thickness and diameter. In one embodiment, abrasive particles are coated onto a plastic base, such as acrylonitrile butadiene styrene (ABS), and the thickness of the abrasive coating is defined by the grit size of the abrasive particles. In a preferred embodiment, the abrasive particles have a grit size of about 120 (approximately 0.0044 inches in diameter, or about 120 microns). Typically, the grit size will be 120 or lower as particles with grit sizes larger than 120 have been shown to cause bruising.

Typically the abrasive tip will have a thickness ranging from 0.5 microns to 150 microns, preferably ranging from 15 microns to 120 microns.

The tip can have any suitable shape or geometry. Typically the tip has a cross-sectional area in the shape of a circle. The size of the tip depends on the size of the area to be permeabilized by abrasion. For example, for applications requiring a small area to be permeabilized, the abrasive tip can have a diameter of up to several micrometers, such as from 1 to 25 micrometers. For applications requiring larger permeabilized areas, the abrasive tip can have a diameter of up to several inches, such as from 0.1 to 5 inches.

iii. Wetting Fluid

Depending on the electrical conductivity of the abrasive tip material, a wetting fluid may or may not be needed to wet the abrasive tip and thereby provide a conductive path to the skin. The wetting fluid may contain any suitable agent, such as water, salts, ionic or non-ionic surfactants, preservatives, alcohol, glycerol, gel, and other similar agents. Various mixtures of these agents may be formulated into wetting fluids with various conductivity levels, depending on the desired application. As used herein a "highly conductive fluid" or a "fluid with a high conductivity" refers to a fluid with a conductivity from about 1,000 to about 100,000 µSiemens/cm. As used herein a "fluid with a low conductivity" refers to a fluid with a conductivity from about 0.1 to about 999 µSiemens/cm. For example, for the external feedback control mechanism, as described in FIG. 1, if the abrasive tip is made of non-conductive material, such as plastic or gritted materials, a highly conductive fluid is needed to provide a conductive path through the skin. If the abrasive tip is made of a conductive material, such as metal, a wetting fluid with either a high conductivity or one with a low conductivity may be used. Alternatively, the system may require no wetting fluid, such as if the metallic abrasive tip itself is sufficiently conductive to provide a conductive path through the pet skin. In a preferred embodiment, a wetting fluid with a conductivity of 500 to 50,000 µSiemens/cm is used with the external feedback control mechanism.

Figure 2B:
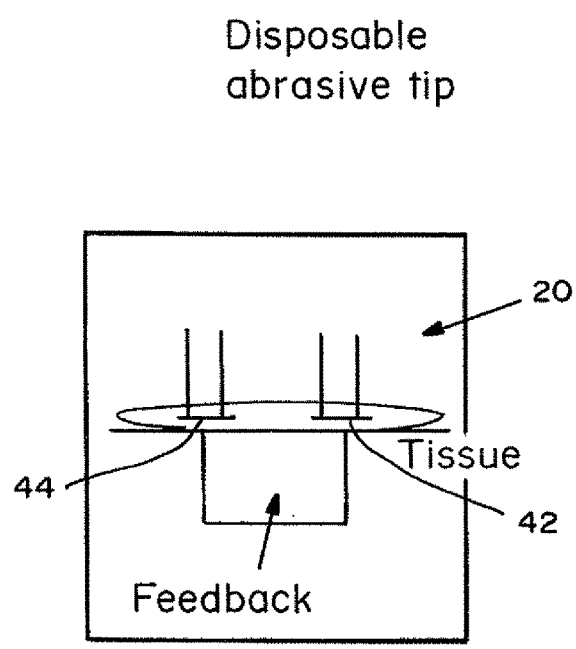

For the internal feedback control mechanism as described in FIGS. 2A and 2B, a wetting fluid with a low conductivity should be used. Wetting fluids with high conductivities should generally be avoided as they are likely to cause a short circuit and improper device function. The abrasive tip illustrated in FIGS. 2A and 2B is typically formed of a non-conductive material. The use of such a wetting fluid provides a low conductivity baseline when the skin is intact, followed by a significant increase in conductivity when the skin site is permeated with the abrasion device.

Preferably the wetting fluid contains water, salts, alcohol, glycerol, non-ionic surfactants, preservatives, polyethylene glycol, and/or mixtures thereof. An example of wetting fluid with a high conductivity contains 0.1-20% (wt/wt) of salts, 0-2% (wt/wt) ionic surfactants, 0-20% (wt/wt) alcohol and 0-1% (wt/wt) preservative in purified water. An example of wetting fluid with a low conductivity contains 0-2% non-ionic surfactants, 0-50% alcohol and 0-1% preservative in purified water.

Optionally, the wetting fluid contains one or more active agents, such as a drug, diagnostic agent or prophylactic agent, to be delivered to the subject. Such a wetting fluid is particularly useful in drug delivery applications.

In one embodiment, the abrasive tip is formed from a non-conductive material and the wetting fluid is a fluid with a low conductivity.

iv. Electrodes

The abrasive tip (20) typically contains a first electrode (42) (also referred to herein as the "source electrode") in electrical contact at a site of interest on the tissue to be permeated and in electrical communication with the motor (50) to provide continuity with the feedback control circuitry. In one preferred embodiment, the abrasive tip either contains a conductive element that serves as a source electrode or is formed of a conductive material (see FIG. 3D), which serves as a source electrode, and the source electrode is in contact with a spring (28) to provide continuity from the abrasive tip (20) to the motor shaft. Although FIG. 3D illustrates the use of an abrasive tip that also serves as the source electrode, the same spring configuration can be used with an abrasive tip foemed of a non-conductive material that contains at least one conductive element inserted therein. In this embodiment, the source electrode is located within the abrasive tip (20) in a position level with the outer surface of the abrasive tip.

The same spring configuration illustrated in FIG. 3D can be used with a device containing an internal control feedback mechanism, such as the device depicted in FIG. 2A.

In some embodiments of the abrasion device that contain an external feedback control mechanism, the abrasive tip does not contain an electrode. In these embodiments, the first electrode (42) (or source electrode) may be located in a locating ring (60) (see e.g. FIG. 1).

The electrode can be made of any suitable conducting material including, for example, metals and conducting polymers. Additionally both electrodes can be designed with any suitable shape that allows the electrodes to contact the skin and electrically communicate with the feedback control circuitry.

Multiple electrodes can be used to achieve more homogeneous skin permeation. To provide accurate electrical reading, the surface of the patient's skin in contact with at least one electrode must be sufficiently permeated, i.e. the stratum corneum should be removed from the site where the electrode is applied.

In a preferred embodiment, the abrasive tip (20) is designed with an internal feedback control mechanism. In this embodiment, the abrasive tip contains two electrodes, which are located within the abrasive tip in a position leveled with the outer surface of the abrasive tip. In this embodiment, the abrasive tip contains both the first, or source, electrode (42) and the second, or return, electrode (44). The electrodes are made of any suitable conducting material including, for example, metals and conducting polymers. For the internal feedback mechanism to function properly in this embodiment, the abrasive tip is preferably formed from a non-conductive material. If a wetting fluid is applied to the abrasive tip, the wetting fluid is preferably a fluid with a low conductivity.

In a preferred embodiment for a device with an external feedback control mechanism, the proximal end (14) of the abrasion device (10) contains two electrodes in a co-axial or concentric arrangement (see FIGS. 3B and 3C). In this embodiment, the proximal end (14) of the abrasion device (10) contains both the first, or source, electrode (42) and the second, or return, electrode (44). Looking at a plan view of the proximal end (14) of the abrasion device, the source electrode is located in the center of the proximal end of the abrasion device. The source electrode is surrounded by a space filled with air (26), which is surrounded by the return electrode (44). FIG. 3B illustrates an embodiment where the abrasive tip is formed of a conductive material and also serves as a source electrode. FIG. 3C illustrates an embodiment where the abrasive tip is formed of a non-conductive material, and the source electrode, typically in the form of a wire, is inserted in the abrasive material.

In the coaxial or concentric arrangement, the second, or return electrode (44) is located in a the outer wall (21) of the proximal end (14) of the hand piece. Looking at a plan view of the proximal end (14) of the abrasion device, the return electrode (44) forms the outer ring of the device (see FIGS. 3B and 3C).

In another embodiment for a device with an external feedback control mechanism, the second, or return, electrode (44) is separated from the controlled abrasion device (see e.g. FIG. 1). The location of the second electrode may be adjacent to or distant from the location of the first electrode.

b. Feedback Control Mechanism

The feedback control mechanism (30) involves the use of (i) a first electrode (42) located at the site of the skin that will be/is being abraded (herein the "site of skin abrasion") to measure periodically or continuously the skin's electrical conductance at the site of skin abrasion, (ii) at least a second electrode (44), which may be located at a site distant from the site of skin abrasion, may be adjacent to the site of skin abrasion or may be in contact with the site of skin abrasion, and (iii) a controller (32). The controller performs mathematical analysis using an appropriate algorithm or signal processing on the conductivity information provided by the electrodes (42 and 44) and calculates the kinetics of the skin conductance. The controller also controls the abrasion device (10).

The dynamic change in the conductance through the skin is measured in real time while the abrasion device is applied to the skin. Signal processing is performed based on the measurement, and the level of skin permeation is controlled by performing a dynamic mathematical analysis. The result of such analysis is used to control the application of the abrasion device to achieve the desired level of skin impedance. The desired level of skin impedance can be set at a predetermined value. Alternatively, the level of skin impedance can be selected based on the desired level of skin integrity, the subject's sensation of discomfort, or the duration of the application.

An example of real time algorithm for controlled skin permeation is described in U.S. Pat. No. 6,887,239 to Elstrom et al., and is demonstrated in FIGS. 4-7. U.S. Pat. No. 6,887,239 to Elstrom et al. describes a general method for controlling the permeability of the skin surface when a site is undergoing a permeation enhancement treatment.

Figure 4:
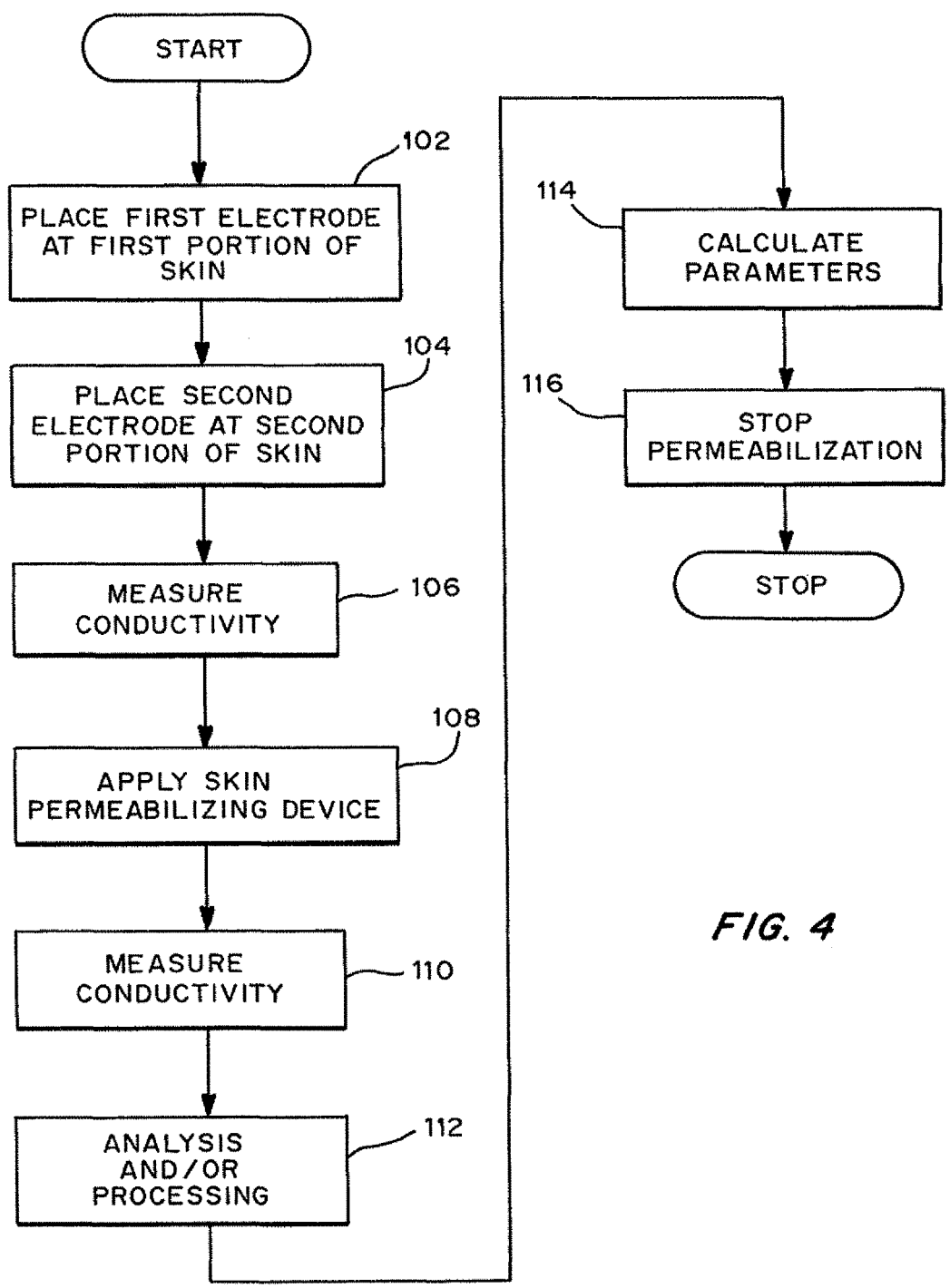
FIG. 4 is a flowchart of a method for controlling abrasion of an area on the surface of the skin to achieve the desired level of permeability.

FIG. 4 is a flowchart of a method for controlling abrasion of an area on the surface of the skin to achieve the desired level of permeability. The skin permeation device referenced in step 108 is the abrasion device described herein. However, alternative permeation devices and methods may be modified to use the controlled feedback mechanism described herein. Alternative permeation methods include tape stripping, rubbing, sanding, abrasion, laser ablation, radio frequency (RF) ablation, chemicals, sonophoresis, iontophoresis, electroporation, and thermal ablation. In step 102, a first, or source, electrode is coupled in electrical contact with a first area of skin where permeation is desired.

Next, in step 104, a second, or return, electrode is coupled in electrical contact with a second area of skin. This second area of skin may be located at a site distant from the site of skin abrasion, may be adjacent to the site of skin abrasion or may be within the site of skin abrasion.

When the two electrodes are properly positioned, in step 106, an initial conductivity between the two electrodes is measured. This may be accomplished by applying an electrical signal to the area of skin through the electrodes. In one embodiment, the electrical signal may have sufficient intensity so that the electrical parameter of the skin can be measured, but have a suitably low intensity so that the electrical signal does not cause permanent damage to the skin, or any other detrimental effects. In one embodiment, an AC source of frequency between 10 to 100 Hz is used to create a voltage differential between the source electrode and the return electrode. The voltage supplied should not exceed 500 mV, and preferably not exceed 100 mV, or there will be a risk of damaging the skin. The current magnitude may also be suitably limited. The initial conductivity measurement is made after the source has been applied using appropriate circuitry. In another embodiment, a resistive sensor is used to measure the impedance of the area of skin at a frequency between 10 and 100 Hz. In another embodiment, dual or multiple measurements with dual or multiple AC source of frequency may be made using similar or dissimilar stimuli. In another embodiment, a 1 kHz source is used. Sources of other frequencies are also possible.

In step 108, the abrasion device is applied to the skin at the first site.

In step 110, the conductivity between the two electrodes is measured. The conductivity may be measured periodically, or it may be measured continuously. The monitoring measurements are made using the same electrode set up that was used to make the initial conductivity measurement.

In step 112, mathematical analysis and/or signal processing may be performed on the time-variance of skin conductance data. Skin conductivity can be measured at set time periods, such as once every second during permeation treatment, or continuously.

After plotting the conductance data, the graph resembles a sigmoidal curve, which can be represented by the following general sigmoidal curve equation (Eq. 1):

$$C = C_i + (C_f - C_i)/(1 + e^{-S(t-t^*)})$$ Eq. 1 where C is current; $C_i$ is current at t=0; $C_f$ is the final current; S is a sensitivity constant; t* is the exposure time required to achieve an inflection point; and t is the time of exposure.

Figure 5:
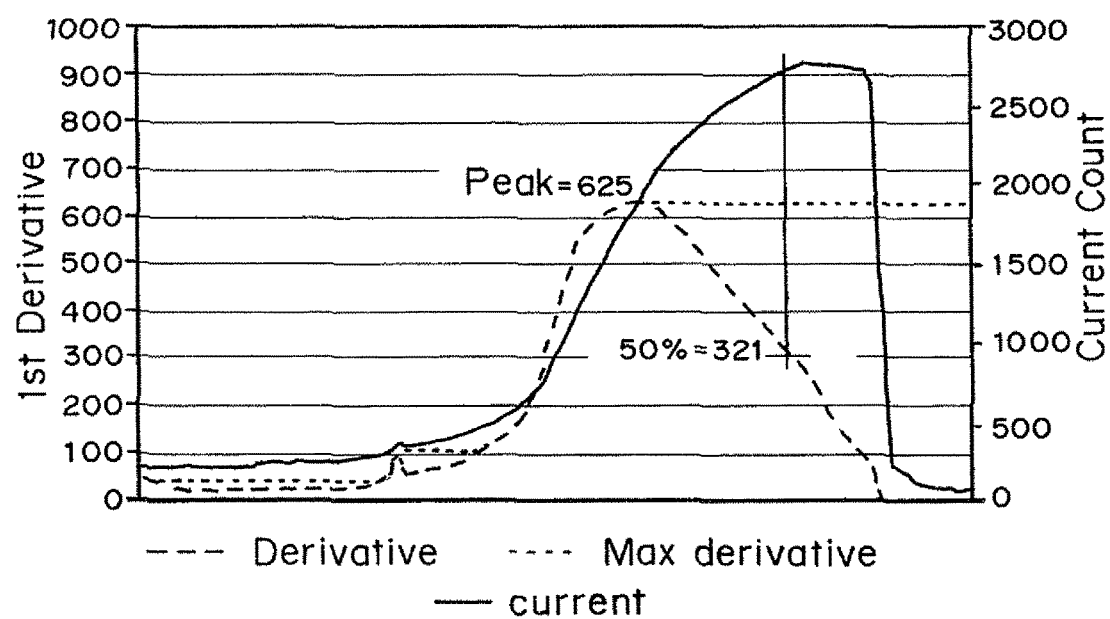
FIG. 5 is a graph of the time variation of skin conductivity (I, in the unit of Counts) during application of a controlled abrasion device to the skin. The solid line is a graph of counts, (1 Count=0.0125 µ-Amps) over time (Seconds) (solid line); the dashed line is a graph of the first derivative of the conductivity curve, i.e. $\Delta I/\Delta T$ (Count/Second) over time (Seconds); the horizontal dotted lines represent the maxima in the first derivative.

FIG. 5 contains a representative set of data in the form of a plot of current over time. FIG. 5 demonstrates the time variation data of skin conductance while being treated with the abrasion device. In FIG. 5, the conductivity (Current Count, the solid line) was measured continuously during a skin permeation procedure on a test subject.

The value of t* in Equation 1 corresponds to the exposure time required to achieve an inflection point (i.e., a point where the slope of the curve changes sign), and corresponds with the peak of the first derivative, which has a value of 625 based on the data represented in FIG. 4.

Figure 6:
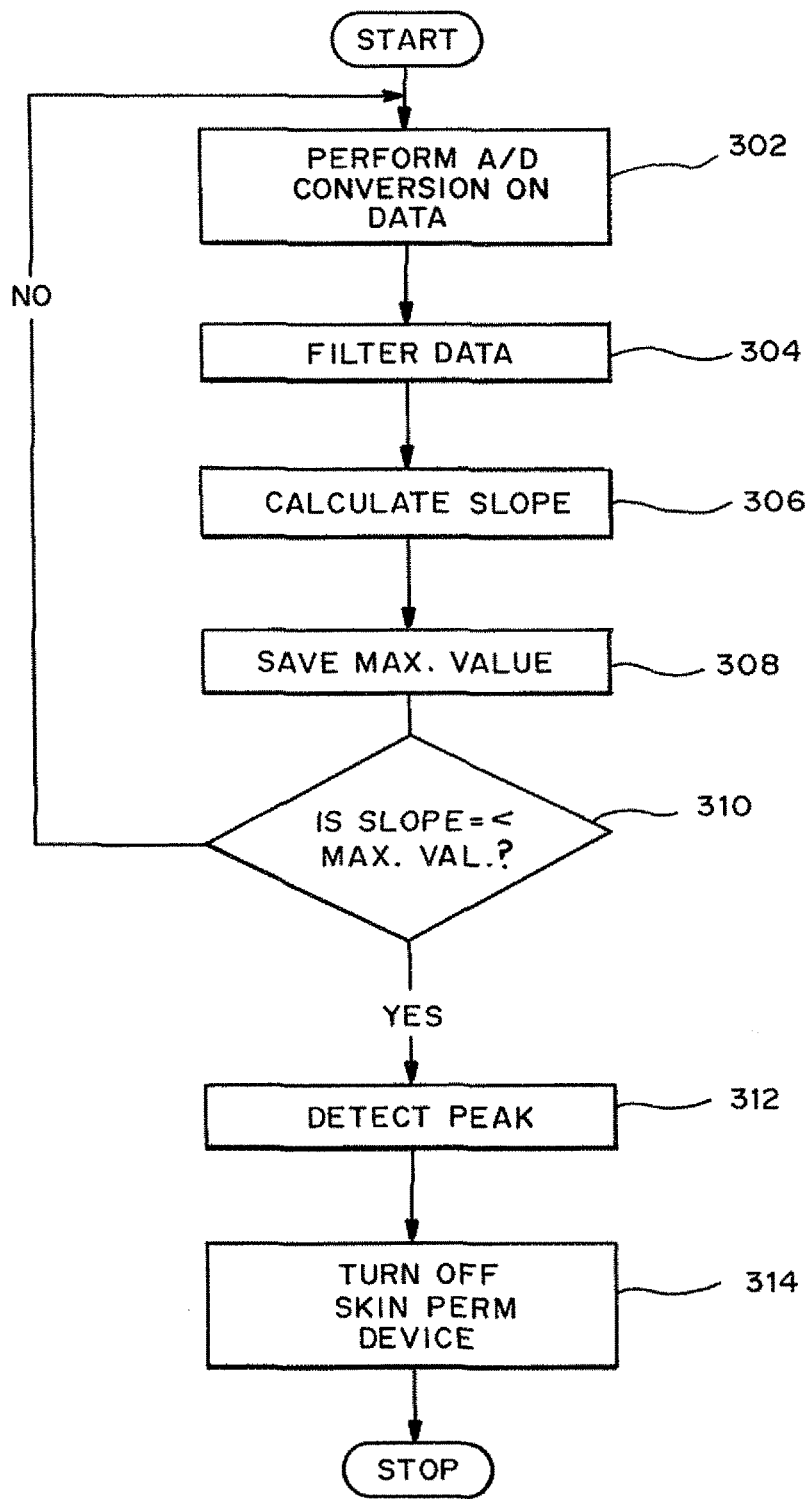
FIG. 6 is a flowchart depicting a method of determining when to terminate the permeation step.
Figure 7A:
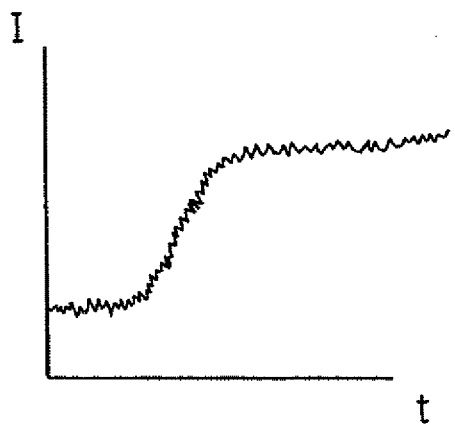
FIGS. 7A, B, and C are representative graphs that correspond with the steps in the flowchart of FIG. 6.
Figure 7B:
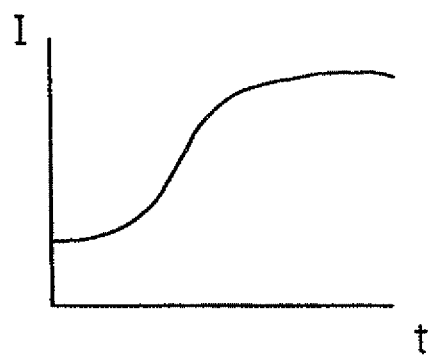
Figure 7C:
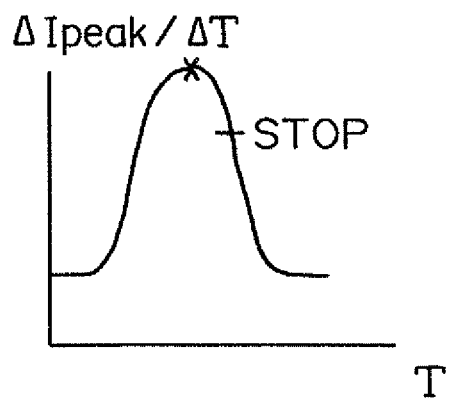

FIG. 6 is a flowchart depicting a method of determining when to terminate the permeation step. FIGS. 7A, B, and C are representative graphs that correspond with the steps in the flowchart of FIG. 6. In FIG. 6, step 302, an A/D conversion is performed on the conductivity data. This results in a graph similar to the one depicted in FIG. 7A. Next, in step 304, filtering is performed on the digital data. As shown in FIG. 7B, the filtered data has a smoother curve than the unfiltered data of FIG. 7A. Next, in step 306, the slope of the curve is calculated. In step 308, the maximum value for the slope is saved. If the current value for the slope obtained during subsequent measurements is greater than the maximum value that is saved, the maximum value is replaced with the current value. Next, in step 310, if the slope is not less than or equal to the maximum value, the process returns to step 302 to wait for a peak. If the slope is less than or equal to the maximum value, in step 312 the process detects a peak, or point of inflection, marked as "X" in FIG. 7C, then, in step 314, the device terminates the application of abrasive force to the skin.

In one embodiment, the detection of the peak may be validated. This additional step may be provided to ensure that the "peak" detected in step 312 was not mere noise, but was actually a peak.

In other embodiments, the abrasive force may continue to be applied even after the inflection point, i.e. "peak", is reached. In another embodiment, the abrasive force is applied until the slope decreases to a certain value. Referring to FIG. 5, after the inflection point is reached, the slope decreases as the abrasive force is applied (see dashed line). Thus, the abrasive force may continue to be applied until the slope decreases by a preset percentage of the maximum of the first derivative of the conductivity curve, such as 50%, or to a predetermined value. As above, this determination is flexible and may vary from individual to individual. Similarly, as shown in FIG. 5, a real time, first derivative of the conductivity curve was calculated (step 306 of FIG. 6) and the maximum was found to be 625 (steps 308 and 312). The offset (i.e. baseline) for this curve was about 17 ($\Delta I/\Delta T$). For the data represented in FIG. 5, if the stopping point for the permeation step is preset at 50% of the maximum of the first derivative of the conductivity curve, the instrument will shut off automatically when the first derivative value reaches 321 (data corrected for offset), indicating that the skin permeation is complete. Other percentages may be used, and the percentage may be based on factors including pain threshold and skin characteristics.

In another embodiment, the stopping point is set to a predetermined period of time. This predetermined period of time may be based on a percentage of the time to reach the inflection point. For example, once the inflection point is reached, the abrasion device continues to be applied for an additional 50% of the time it took to reach the inflection point (see e.g. FIG. 5). Thus, if it took 14 seconds to reach the inflection point, abrasion is applied for an additional 7 seconds (not shown in figure). Other percentages may be used, and the percentage may be based on factors including pain threshold and skin characteristics.

In another embodiment, the current at the inflection point is measured, and then application of the abrasive tip is continued for a preset percentage of this current. For example, if the inflection point is reached at 40 µamps, and the abrasive tip is continued for a present percentage of the current at the inflection point, such as 10% of the current at the inflection point, the abrasive tip will be applied until a total of 44 µamps of current is reached. Again, this determination is flexible and may vary from individual to individual.

Referring to FIG. 4, in step 114, the parameters describing the kinetics of skin impedance (or conductance) changes are calculated. These parameters include, inter alia, skin impedance, the variation of skin impedance with time, initial skin impedance, moving average of skin impedance, maximum skin impedance, minimum skin impedance, any mathematical calculation of skin impedance, final skin impedance, skin impedance at inflection time, current count, final current, exposure time to achieve the inflection time, etc.

In step 116, the skin permeation device applied in step 108 is terminated when desired values of the parameters describing skin conductance are achieved.

c. Electrical Motor

An electrical motor (50) is located in the hand piece (12). The abrasive tip (20) connects directly or indirectly with the motor (50), which allows the motor to move, such as by oscillation or rotation, the abrasive tip, when the controlled abrasion device is turned on.

Electrical motors are available in two primary classes: AC and DC motors. They are either rotary or linear.

Preferably the motor (50) is a rotary, DC motor. In a preferred embodiment, the motor is a rotary, brushed, DC motor due to its relative ease of use with standard power supplies (i.e. direct current batteries) as compared to "brushless" motors that utilize more expensive rare earth metals in their construction, and availability. However, brushless motors may also be used with the device.

The motor can produce a variety of motion patterns, such as linear, vibration, concentric, co-axle, and off-axle motions. Additionally, the motor can produce a variety of motion speeds, such as ranging from 0.01-10,000 rps or Hz.

d. Means for Providing Force to the Abrasive Tip

In the preferred embodiment, the controlled abrasion device contains one or more means for providing a force to the abrasive tip to ensure that the abrasive tip remains in contact with the skin when the controlled abrasion device is turned on. Suitable means include a spring (16) loaded motor shaft or coupler to provide a downward (i.e. towards the skin surface) force on the abrasive tip when it is in contact with the skin surface (see FIG. 3A).

As shown in FIG. 3A, the spring (16) contracts when the abrasive tip is pressed against the skin. When the spring contracts, the proximal end (14) of the hand piece (12) moves towards the surface of the skin, causing the return electrode (44) to contact the skin. Thus, in this position, the source electrode (42), the abrasive tip (20) and the return electrode (44) are in contact with the skin's surface.

e. Return Electrode

As noted above, the device typically contains at least one second electrode, which serves as a return electrode (44) (see e.g. FIGS. 1, 2A, 2B, and 3A-D). For devices designed to contain an internal feedback control mechanism, the return electrode is located in the abrasive tip (see FIGS. 2A and 2B). However, if the device is designed to contain an external feedback control mechanism, the return electrode is placed at a site on the skin surface that is different from the site of skin abrasion (see FIG. 1 and FIGS. 3A-C). The return electrode may be placed at a site on the skin that is distant from the site of skin abrasion (see e.g. FIG. 1) Alternatively the return electrode may be placed at a site on the skin that is adjacent to the site of skin abrasion (see e.g. FIG. 3A-C). As shown in FIG. 1, the return electrode (44) is in electrical contact with the controller, and is in electrical contact with the first electrode (42). As shown in FIG. 3A, the return electrode (44) may be integrated in the device. The return electrode (44) is in electrical contact with the controller, and is in electrical contact with the first electrode (42).

The reliability of such devices with a return electrode that is at a site distant from the site to be permeated can be questionable since the return electrode can provide accurate feedback only when it is located on a skin site which has sufficient electrical conductivity. Thus, in the preferred embodiment, the return electrode is located on the abrasive tip. In this embodiment, the return electrode is also in contact with the skin to be permeated.

In a preferred embodiment for the external feedback control mechanism, the return electrode (44) in the coaxial or concentric arrangement with the first electrode. In this embodiment, the second, or return electrode (44) is located in a the outer wall (21) of the proximal end (14) of the hand piece and forms a outer ring surrounding the source electrode and abrasive tip (see FIGS. 3B and 3C). Moving outward from the center of the device, the abrasive tip and source electrode are surrounded by a plastic tube (24) to which the abrasive tip is attached, the plastic tube is surrounded by a void or space filled with air (26), the void is surrounded by a plastic cup or cone (27), which is surrounded by a conductive material that serves as the return electrode (44).

II. System for Analyte Sensing

The controlled abrasion device described herein can be combined with an analyte sensor to detect the level of one or more analytes of interest present in a body fluid. The body fluid may be extracted by physical forces, chemical forces, biological forces, vacuum pressure, electrical forces, osmotic forces, diffusion forces, electromagnetic forces, ultrasound forces, cavitation forces, mechanical forces, thermal forces, capillary forces, fluid circulation across the skin, electro-acoustic forces, magnetic forces, magneto-hydrodynamic forces, acoustic forces, convective dispersion, photo acoustic forces, by rinsing body fluid off skin, and any combination thereof. The body fluid may be collected by a collection method including absorption, adsorption, phase separation, mechanical, electrical, chemically induced, and a combination thereof. The presence of an analyte may be sensed by a sensing method including electrochemical, optical, acoustical, biological, enzymatic technology, and combinations thereof.

For example, after using the controlled abrasion device to achieve the desired level of permeability at a skin site, an analyte sensor, such as a glucose sensor device, may be placed over the skin site that has been treated by the abrasion system. The glucose sensor functions by receiving glucose flux continuously through the skin. In response, the device provides an electrical signal, in nanoamperes (nA), which is calibrated to the reference blood glucose (BG) value of the subject using a commercial finger-sticks glucose meter. The combination of the controlled abrasion system with a blood glucose sensor is described below in the examples.

Although the above example refers to glucose sensing, other analytes can be analyzed using the same method. The analyte may be any molecule or biological species that is present in a biological fluid, such as blood, plasma, serum or interstitial fluid. The analyte to be monitored can be any analyte of interest, including, but not limited to glucose, lactate, blood gases (e.g. carbon dioxide or oxygen), blood pH, electrolytes, ammonia, proteins, biomarkers or any other biological species that is present in a biological fluid.

III. System for Drug Delivery

The controlled abrasion device described herein can be combined with a drug delivery composition or device to transdermally deliver drug to a subject. The drug may be any suitable therapeutic, prophylactic, or diagnostic molecule or agent, in any suitable form. The drug may be dissolved or suspended in a liquid, solid, semi-solid, or encapsulated and/or distributed in or within micro or nanoparticles, emulsion, liposomes, or lipid vesicles. Drug delivery may occur into blood, lymph, interstitial fluid, cells, tissues, and/or organs, or any combination thereof. The drug is typically delivered systemically.

For example, after using the controlled abrasion device to achieve the desired level of permeability at a skin site, drug delivery composition or device, such as an ointment, cream, gel or patch containing the drug to be administered, may be placed over the skin site that has been treated by the abrasion system.

Alternatively, the drug may be included in a wetting fluid that is applied to the abrasive tip. In this embodiment, the drug may be administered simultaneously as the surface is being abraded.

IV. Kits

Kits for controlled abrasion include the abrasion device described above and one or more abrasive tips. Optionally, the kit includes a wetting fluid, which is packaged in an appropriate container, to be added to the abrasive tip. In another embodiment, the wetting fluid is pre-applied to the one or more abrasive tips and which are packaged to maintain the moisture in the abrasive tip. In yet another embodiment, the kit includes one or more pre-moistened wipe containing the wetting fluid.

If the device utilizes disposable abrasion tips, the kit preferably also contains one or more disposable plastic cups or cones (27). Preferably the disposable abrasive tip is attached to a tube (24) that is designed to mate with and connect to the hand piece.

If the abrasion device is designed to contain an external feedback control mechanism, the kit also includes one or more return electrodes.

V. Methods of Reducing Skin Impedance

A. Controlled Abrasion Device

The controlled abrasion device described herein can be applied to the surface of a subject's skin to reduce the skin impedance by 30 times or more compared to the skin impedance measured following wetting with pure water in the absence of a skin permeation treatment. Typical skin impedance measurements following wetting with pure water in the absence of a skin permeation treatment are about 300 k-ohms or above, when measured by placing two electrodes within a distance of approximately 1 cm on the wetted skin. Following treatment of the same area of the skin using the controlled abrasion device, the impedance value can be reduced to about 10 k-ohms or lower.

The abrasive tip is typically applied for a short period of time for up to 90 seconds, such as from 1 to 30 seconds, preferably from 5 to 25 seconds. The desired level of skin impedance (or conductance), and thus the resulting permeability of the treated site, can be set at a predetermined value. Alternatively, the level of skin impedance (or conductance) can be selected based on the desired level of skin integrity, the subject's sensation of discomfort, or the duration of the application, as described above.

Once the desired level of permeability has been reached, the abrasion device is removed and either a drug delivery composition or device or an analyte sensor is applied to the treated site. Drug delivery can proceed immediately, as soon as the drug delivery system is applied to the abraded skin. In a similar manner, the analyte can diffuse from the body and into the analyte sensor as soon as the analyte sensor is applied to the skin. However, accurate values of the analyte are usually not available during the "warm-up" period, i.e. the time it takes for the transdermal analyte flux to reach equilibration, the sensor to consume skin-borne analyte and possibly other interference species, and the physical coupling of sensor to the skin sites to become stable. The warm-up period typically lasts for about 1 hour following application of the analyte sensor to the prepared site.

Following application of the abrasion device, the site typically remains permeable for up to 24 hrs, and in some embodiment for up to 72 hrs.

B. Other Permeation Devices

Other permeation devices and techniques may be used in place of the controlled abrasion device described herein to achieve a desired level of skin permeation. For example, the feedback control mechanism can be combined with other skin preparation methods, such as tape stripping, rubbing, sanding, abrasion, laser ablation, radio frequency (RF) ablation, chemicals, sonophoresis, iontophoresis, electroporation, and thermal ablation.

EXAMPLES

Example 1

Comparison of Two Skin Permeation Methods: Sonophoresis and Abrasion

In a 6-subject, 24-hour study the performance of the abrasion method was compared to a sonophoresis method described in U.S. Pat. No. 6,887,239 to Elstrom et al. using the same control algorithm as indicated in FIG. 4. Each subject had one abraded site and one sonicated site on chest or abdomen sites.

For the controlled abrasion system, the abrasion device described in FIG. 1 was applied to the patients' skin for 5 to 25 seconds, until the conductivity feedback threshold was attained (as described previously in section I.b. Feedback Control Mechanism).

For the controlled sonophoresis system, ultrasound at a frequency of 55 kHz was applied to the patients' skin for 5 to 30 seconds using the Sontra SonoPrep® ultrasonic skin permeation device. The ultrasound was applied until the conductivity feedback threshold was attained (as described previously in section I.b. Feedback Control Mechanism).

Glucose sensor units were placed on each of the two target skin sites prepared by controlled abrasion or sonophoresis. Throughout the course of the study, reference finger-stick blood glucose ("BG") samples were taken during the waking hours, at hourly intervals, or at 15-minute intervals near meal times, and were correlated to the electrical signal of the sensor.

Analysis of this correlation provides information about device accuracy, consistency and effective length of performance.

Figure 8:
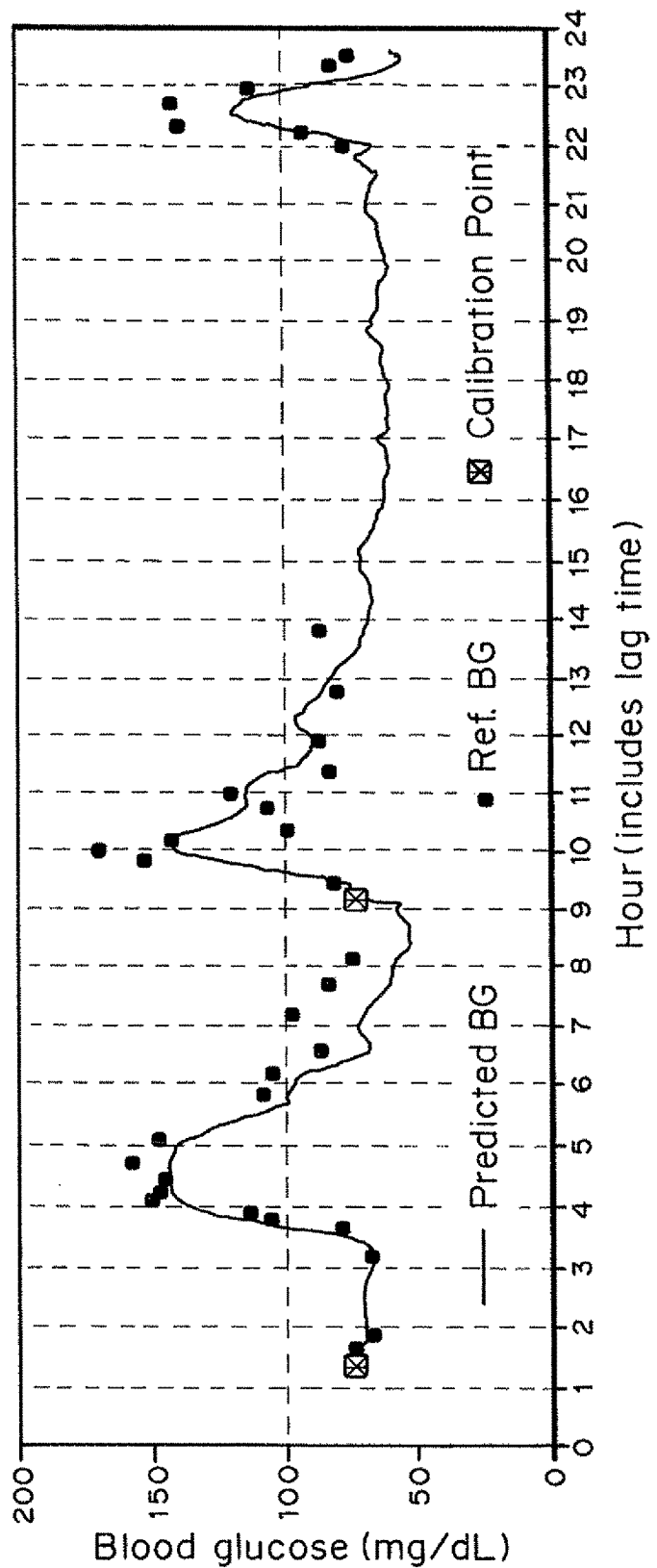
FIG. 8 is a graph of blood glucose level (mg/dL) versus time (hours) of the results obtained using the abrasion system on a test subject to permeate the skin, followed by continuous transdermal glucose monitoring.

FIG. 8 is a graph of the results obtained using the abrasion system on a test subject to permeate the skin followed by continuous transdermal glucose sensing. Table 1 shows the results of the direct comparison of abrasion to sonication as the means of skin permeation for continuous glucose monitoring. Table 1 shows the average values based on the data obtained from six subjects.

TABLE 1

| | | Statistical Results | | | | | |
|---|---|---|---|---|---|---|---|
| Technique | n | Baseline (nA) | Lag Time (min) | 12 hr MARD 1 cal | 24 hr Drift (%) | 24 hr MARD 2-3 cal | % A Region |
| Abrasion | 6 | 395 | 14 | 18.4 | 31 | 11.7 | 85 |
| Ultrasound | 6 | 409 | 10 | 16.2 | 26 | 13.1 | 80 |

The reference blood glucose (Ref BG) values were measured by a commercial blood glucose meter using finger sticks. Two calibrations were done to the glucose sensor based on Ref BG values at 1.2 and 9.1 hours (labeled as "calibration points" on FIG. 8). The close proximity of the sensor glucose reading (Predicted BG) to the reference blood glucose (Ref BG) indicates good accuracy of the transdermal glucose sensor. The 24-hour Mean Absolute Relative Difference (MARD) between the Ref BG and the Predicted BG was 11.9 mg/dl.

For permeation using the controlled abrasion device, the average 24-hr MARD was 11.7 mg/dl with a signal drift of 31%. For the controlled sonophoresis system, the average 24-hr MARD was 13.1 mg/dl with a signal drift of 26%. Thus the controlled abrasion device provided tracking (nA to BG correlation) that was comparable to or in some cases better than the sonophoresis system, in terms of warm-up period (one hour), accuracy (MARD, Mean Absolute Relative Difference, between sensor predicted glucose and reference BG, in the unit of mg/dl), and drift (time-dependent % deviation of sensor glucose and reference BG), and percentage of data distribution in the "A region" based on Clarke Error Grid analysis ("% A Region").

Example 2

Lowering Impedance of Skin Following Application of Abrasion Device

When human skin is wetted by pure water, the impedance value is usually 300 k-ohms or above, when measured by placing two electrodes within a distance of approximately 1 cm on the wetted skin. However, when the same area was treated by with a controlled abrasion device using a control algorithm as shown in FIG. 1, by placing the device on the skin surface for 5 to 25 seconds and obtaining the impedance value simultaneously with the application of the device, the impedance value was significantly reduce to about 10 k-ohms or lower. In this study, the abrasive tip contained white aluminum oxide (120 grit) coated onto an ABS base.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A controlled abrasion device comprising a hand piece, an abrasive tip, a feedback control mechanism, and an electrical motor, wherein the feedback control mechanism comprises (a) a source electrode that applies an electrical signal to an area of skin, (b) a return electrode and (c) a controller, and wherein the feedback control mechanism measures in real time dynamic change of an electrical parameter at a skin site and calculates a rate of change in the electrical parameter over time when the device is applied to the skin to control the level of skin abrasion, wherein the electrical signal does not cause permanent damage to the skin, and wherein, after the rate of change in the electrical parameter reaches a maximum value, the controller stops the abrasion when the rate of change in the electrical parameter decreases to a set percentage of the maximum value or a preset value that is less than the maximum value.

2. The device of claim 1, wherein the feedback control mechanism is an internal feedback control mechanism.

3. The device of claim 1, wherein the return electrode is located at the proximal end of the hand piece.

4. The device of claim 1, wherein the abrasive tip comprises a conductive material.

5. The device of claim 4, wherein the abrasive tip is the source electrode.

6. The device of claim 1, wherein the abrasive tip is a disposable abrasive tip.

7. The device of claim 1, wherein the source electrode and the return electrode are in electrical communication with the controller.

8. The device of claim 1, wherein the source electrode is located in the abrasive tip.

9. A method for reducing the impedance of a skin site comprising
applying an abrasive tip of a controlled abrasion device to the skin site, wherein the device comprises a hand piece, the abrasive tip, a feedback control mechanism, and an electrical motor, wherein the feedback control mechanism comprises (a) a source electrode that applies an electrical signal to an area of the skin site, (b) a return electrode and (c) a controller,
wherein the feedback control mechanism measures in real time dynamic change of an electrical parameter at a skin site and calculates a rate of change in the electrical parameter over time when the device is applied to the skin to control the level of skin abrasion, wherein the electrical signal does not cause permanent damage to the skin,
turning the electrical motor on,
measuring the electrical parameter of the skin site, and
after the rate of change in the electrical parameter reaches a maximum value, stopping the abrasion when the rate of change in the electrical parameter decreases to a set percentage of the maximum value or a preset value that is less than the maximum value.

10. The method of claim 9, wherein the step of measuring the electrical parameter of the skin site comprises applying an electrical current between the source electrode and the return electrode.

11. The method of claim 9, wherein the return electrode is located in an outer wall of the proximal end of the hand piece.

12. The method of claim 9, further comprising the steps of analyzing the electrical parameter, and controlling one or more of the duration, speed or force of the abrasive tip based on results of the analyzing step.

13. The method of claim 12, wherein the step of analyzing the electrical parameter comprises processing the measured electrical parameter to derive a current count or impedance value of the skin site.

14. The method of claim 12, wherein the step of controlling comprises turning off the motor when the analyzed electrical parameter is equal to or exceeds a predetermined value.

15. The method of claim 14, further comprising the steps of removing the abrasive tip from the skin site, and thereafter placing an analyte sensor or drug delivery composition or device on the skin site.

16. The method of claim 14, further comprising the steps of removing the abrasive tip from the skin site, and thereafter placing an analyte sensor on the skin site, wherein the analyte sensor is capable of sensing an analyte selected from the group consisting of glucose, lactate, blood gases, blood pH, electrolytes, ammonia, proteins and biomarkers.

17. The method of claim 9, wherein the step of measuring the electrical parameter of the skin site is performed continuously during the step of applying the abrasive tip to the skin site.

18. A kit for reducing the impedance of a skin site comprising a controlled abrasion device, and at least one abrasive tip,
wherein the abrasion device comprises a hand piece, a feedback control mechanism, and an electrical motor, wherein the feedback control mechanism comprises (a) a source electrode that applies an electrical signal to an area of the skin, (b) a return electrode and (c) a controller, and
wherein the feedback control mechanism measures in real time dynamic change of an electrical parameter at the skin site and calculates a rate of change in the electrical parameter over time when the device is applied to the skin to control the level of skin abrasion,
wherein the electrical signal does not cause permanent damage to the skin, and
wherein, after the rate of change in the electrical parameter reaches a maximum value, the controller stops the abrasion when the rate of change in the electrical parameter decreases to a set percentage of the maximum value or a preset value that is less than the maximum value.

19. The kit of claim 18, wherein the proximal end of the device comprises the return electrode.

20. The kit of claim 18, further comprising a wetting fluid.

* * * * *